| | | | |
|---|---|---|---|
| United States Patent [19] | | [11] | 4,254,017 |
| Dworkin et al. | | [45] | Mar. 3, 1981 |

[54] ORGANOTIN MERCAPTOALKANOL ESTERS AND ALKOXIDES CONTAINING SULFIDE GROUPS

[75] Inventors: Robert D. Dworkin, Old Bridge; William A. Larkin, Morristown, both of N.J.

[73] Assignee: M&T Chemicals Inc., Woodbridge, N.J.

[21] Appl. No.: 959,518

[22] Filed: Nov. 13, 1978

[51] Int. Cl.[3] .......................... C08K 5/57; C07F 7/22
[52] U.S. Cl. .......................... 260/45.75 S; 260/429.7
[58] Field of Search ............ 260/429.7, 429.5, 45.75 S

[56] References Cited

U.S. PATENT DOCUMENTS

| | | | |
|---|---|---|---|
| 2,872,468 | 2/1959 | Leistner et al. | 260/429.7 |
| 3,396,185 | 8/1968 | Hechenbleikner et al. | 260/429.7 |
| 3,565,930 | 2/1971 | Kauder et al. | 260/429.7 |
| 3,565,931 | 2/1971 | Brecker | 260/429.7 |
| 3,979,359 | 9/1976 | Kugele et al. | 260/429.7 X |
| 4,062,881 | 12/1977 | Kugele | 260/429.7 |
| 4,113,678 | 9/1978 | Minagawa et al. | 260/429.7 X |
| 4,118,371 | 10/1978 | Kugele | 260/429.7 |
| 4,124,618 | 11/1978 | Dworkin et al. | 260/429.7 |
| 4,134,878 | 1/1979 | Burley et al. | 260/429.7 |

*Primary Examiner*—Helen M. S. Sneed
*Attorney, Agent, or Firm*—Stanley A. Marcus; Donald G. Marion; Robert Spector

[57] ABSTRACT

This invention relates to novel organotin compounds containing at least one sulfur atom that is bonded exclusively to tin or to tin and hydrogen. The compounds are derivatives of mercaptoalkanols, which are present as the free alcohols, as esters of polycarboxylic acids, esters of acids containing specified non-metallic elements or as alkoxides of specified metallic elements. The compounds are effective catalysts for a variety of reactions and impart heat stability to halogen-containing resins.

20 Claims, No Drawings

ORGANOTIN MERCAPTOALKANOL ESTERS AND ALKOXIDES CONTAINING SULFIDE GROUPS

BACKGROUND OF THE INVENTION

This invention relates to a novel class of organotin compounds that are effective heat stabilizers for halogen-containing resins. This invention further relates to novel organotin compounds containing at least one sulfur atom that is bonded exclusively to tin or to tin and hydrogen. The compounds are derivatives of mercaptoalkanols, which are present as the free alcohols, as esters of polycarboxylic acids, esters of acids containing specified non-metallic elements or as alkoxides of specified metallic elements.

Organotin derivatives of mercaptoalkanols and mercaptoalkanol esters are disclosed in the prior art. U.S. Pat. No. 2,731,489 to Best teaches that organotin derivatives of mercaptoalkanol esters derived from monocarboxylic acids are effective stabilizers for vinyl chloride polymers. Kugele in U.S. Pat. No. 4,062,881 teaches that the performance of this type of stabilizer can be improved and the objectionable odor considerably reduced by introducing sulfide or polysulfide groups that are bonded exclusively to the same or different tin atoms.

It has now been found that the efficacy of many of the organotin stabilizers disclosed in the aforementioned Kugele and Best patents can be significantly increased if the hydroxyl group of the mercaptoalkanol is present as the free alcohol or is reacted to form (1) an ester of a polycarboxylic acid that is further esterified with at least one additional mercaptoalkanol group, (2) a derivative of a silicon-, phosphorus-, or boron-containing compound, or (3) an alkoxide of an aluminum- or titanium-containing compound.

SUMMARY OF THE INVENTION

This invention provides organotin compounds containing (a) at least one tin atom having either (1) one or two hydrocarbyl groups containing from 1 to 20 carbon atoms or (2) one or two carboalkoxyhydrocarbyl or ketohydrocarbyl groups containing at least four carbon atoms, said groups being bonded to tin through carbon;

(b) at least one mercaptoalkanol residue bonded to tin through the sulfur atom of said residue, the oxygen atom of said residue forming a link to hydrogen, to a hydrocarbyl group, to the residue obtained by removal of the hydroxyl portion of the carboxy (—COOH) group of a polycarboxylic acid, a hydroxypolycarboxylic acid or to an element selected from the group consisting of aluminum, boron, phosphorus, silicon, and titanium with the proviso that any polycarboxylic acid is bonded to at least two mercaptoalkanol residues through an oxygen atom of said residues and a carboxyl group of said polycarboxylic acid;

(c) up to 52% by weight of tin and (d) up to 63% by weight of sulfur.

DETAILED DESCRIPTION OF THE INVENTION

The organotin compounds of this invention can be represented by the following formulae:

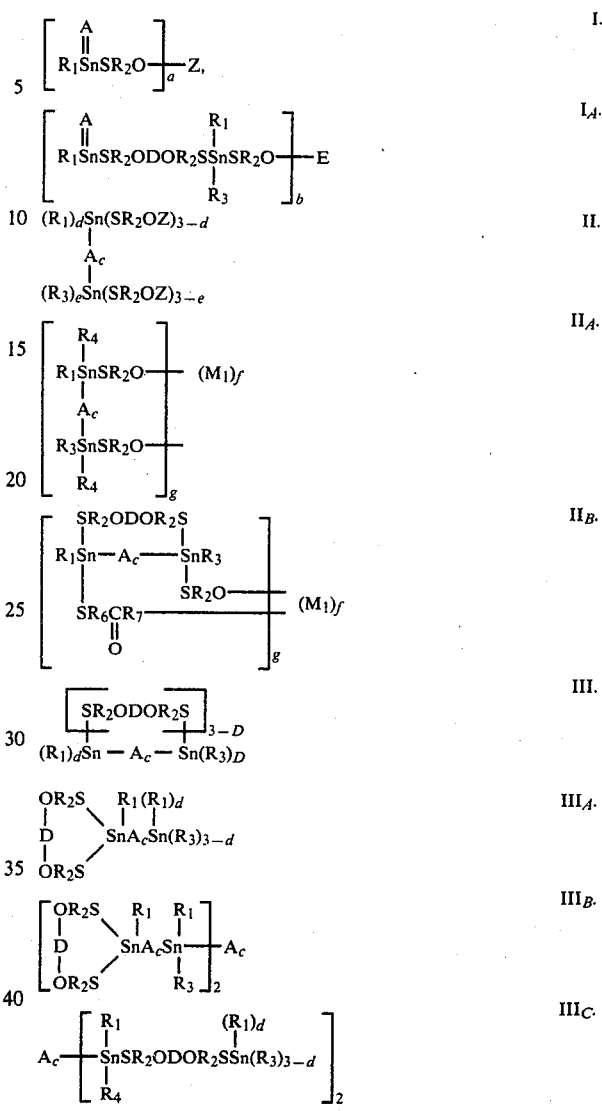

In the preceding formulae $R_1$ is selected from the group consisting of hydrocarbyl (i.e. alkyl, cycloalkyl, aryl, alkaryl and aralkyl), carboalkoxyhydrocarbyl and ketohydrocarbyl. The alkyl portion of any group represented by $R_1$ contains from 1 to 20 carbon atoms. If more than one $R_1$ is present on any tin atom, i.e. d is 2, the second $R_1$ group can optionally represent halogen (chlorine, bromine or iodine), —OH, —SH, the residue obtained by removal of the active hydrogen from the mercapto group of an ester derived from a mercaptocarboxylic acid and a mono- or polyhydric alcohol wherein said ester is bonded to tin through sulfur, the residue obtained by removal of the hydrogen from the mercapto group of a mercaptan, a mercaptoalkanol or an ester derived from a mercaptoalkanol and a mono- or polycarboxylic acid, or the residue obtained by removal of the hydrogen from the carboxy (—COOH) group of a monocarboxylic acid or the carboxy group of a partial ester of a polycarboxylic acid.

$R_2$ represents an alkylene or arylene group that may optionally contain one or more groups represented by the formula —OX wherein X represents hydrogen or $M_1$.

$R_3$ can be selected from the same group as $R_1$ or $R_3$ can represent $R_4$ or $-SR_2OZ$ wherein $R_2$ is as defined hereinbefore and $Z$ will be defined subsequently.

$R_6$ represents alkylene containing from 1 to 20 carbon atoms and $R_7$ represents the residue obtained by removing the hydrogen atom from at least two of the hydroxyl groups of a polyfunctional alcohol containing from 2 to 4 hydroxyl groups.

The group represented by E is selected from the same group as $M_1$ or is $$-OCQCO-$$

and D is $$-OCQCO-.$$

The valence of the E group (represented by b) is from 2 to 4. The subscripts d, e and f in the foregoing formulae are each 1 or 2 and g is 1, 2, 3 or 4.

In one embodiment of the present class of compounds two $R_3$ groups, two $R_1$ groups or and $R_1$ and an $R_3$ group are joined to form the residue of a mercaptoacid, $$-SR_6CO-,$$
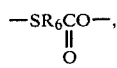

or a di- or polycarboxylic acid, $$-OCQCO-.$$

$R_4$ is selected from the same group as $R_1$ or is $AR_5$, halogen or pseudo-halogen, A is oxygen or sulfur and c is the integer 1 when A is oxygen or an integer from 1 to 10 when A is sulfur. When A is sulfur $R_5$ is $-R_1\text{OCOOR}_{11}$, $$-CR_{12}, -CR_{12},$$
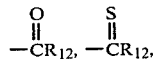

$-R_2OZ$, $-R_2OE$, $-R_2OM_1$, $-SnR_{13}R_{14}R_{15}$ or a hydrocarbyl selected from the same group as $R_1$. When A is polysulfide $R_5$ is $-SnR_{13}R_{15}$. When A is oxygen $R_5$ is $$-CR_{12}, -CQ\ COR_9\ \text{or}\ -CR_{18}SSnR_{13}R_{14}R_{15}.$$
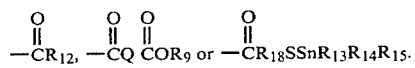

In the foregoing formulae $R_{10}$ represents an alkylene radical containing from 1 to 20 carbons that is optionally substituted with $-COOR_{11}$ or with one or more halogen atoms or hydroxyl groups, $R_{11}$ and $R_{12}$ are hydrocarbyl, which is defined as including alkyl, alkenyl, aryl, cycloalkyl, aralkyl and alkaryl wherein the alkyl portion of any of these groups contains from 1 to 20 carbon atoms and any alkenyl groups contain from 2 to 20 carbon atoms. The $R_{13}$, $R_{14}$ and $R_{15}$ groups that are bonded to tin are selected from the same group as $R_1$. Preferably not more than two of $R_{13}$, $R_{14}$ and $R_{15}$ are hydrocarbyl or substituted hydrocarbyl. This is particularly true when the hydrocarbyl is alkyl containing from 1 to 6 carbon atoms, since the resultant compound may exhibit a relatively high toxicity and relatively low efficacy as a stabilizer. $R_{18}$ is alkylene (including alkylidene) and contains from 1 to 20 carbon atoms, one or more of which may be substituted with a halogen atom or a hydroxyl group.

A characteristic feature of the present compounds is that if the hydroxyl group or groups of a mercaptoalkanol residue is esterified, the free acid must contain at least 2 carboxyl groups which are subsequently reacted with a mercaptoalkanol during preparation of the present compounds. Any remaining carboxyl groups are reacted with a mercaptoalkanol or a mono- or dihydric alcohol.

A second feature which characterizes the present compounds is the presence of a mercaptoalkanol residue, represented in the foregoing formula by $-SR_2O-$. In the simplest form of the present compounds Z is hydrogen and the compounds exhibit the formula

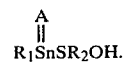
$$R_1SnSR_2OH.$$

A specific example of such a compound is butyltin-β-hydroxyethyl mercaptide sulfide that exhibits the formula

$$n\text{-}C_4H_9SnSCH_2CH_2OH.$$

Alternatively the hydroxyl portion of the mercaptoalkanol residue can be reacted with a polycarboxylic acid, a partial ester thereof, the combination of an alkali metal and an organic halide or specific compounds of phosphorus, silicon, boron, aluminum or titanium. In these instances Z represents a substituted or unsubstituted hydrocarbyl group, including alkyl, aryl, aralkyl, cycloalkyl, hydroxyalkyl and hydroxyalkenyl or a group represented by one of the following formulae:

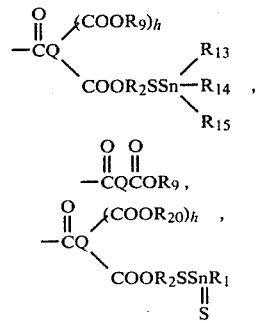

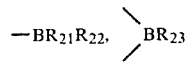
$$-BR_{21}R_{22}, \quad \diagdown BR_{23}$$

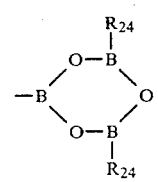

-continued $$\left[\left(B\begin{array}{c}OCH_2CH_2\\ \diagdown\\ \diagup\\ OCH_2CH_2\end{array}N-CH_2\right)_2\right]_a$$

$$-AlR_{25}R_{26}$$

$$-Si(R_{27})_3$$

$$-Ti(OR_{28})_3$$

$$-P(R_{29})_2$$

$$-PR_{30}$$

$$\left(\begin{array}{c}O\\ \|\\ PH\end{array}\right)_a$$

$$\begin{array}{c}O\\ \|\\ -PH\\ |\\ OR_{31}\end{array}$$

$$\begin{array}{c}-PCl_2\\ \|\\ S\end{array}$$

$$\left(\begin{array}{c}PCl\\ \|\\ S\end{array}\right)_a$$

$$\left[\left(\begin{array}{c}P-S\\ \|\\ S\end{array}\right)_m M_2\right]_a$$

$$\left(\begin{array}{c}OR_{31}\\ |\\ P-S\\ \|\\ S\end{array}\right)_m M$$

$$\left(\begin{array}{c}PSCH-COOR_{32}\\ \|\ |\\ S\ CH_2COOR_{32}\end{array}\right)_a$$

$$\begin{array}{c}OR_{30}\\ |\\ -PSCHCOOR_{32}\\ \|\ |\\ S\ CH_2COOR_{32}\end{array}$$

$$\left[\begin{array}{c}P-O-\langle\;\rangle-R_{33}\\ \|\\ S\end{array}\right]_a$$

$$\begin{array}{c}O\\ \|\\ -C-Q\end{array}\left\{COO\left[\begin{array}{c}R_{34}\\ |\\ C\\ |\\ R_{35}\end{array}\right]_n\left[\begin{array}{c}R_{36}\\ |\\ C\\ |\\ R_{37}\end{array}\right]_p\begin{array}{c}R_{13}\\ |\\ S-Sn-R_{14}\\ |\\ R_{15}\end{array}\right\}_q$$

In the foregoing formulae h represents the integer 0, 1 or 2; n and p each represent an integer from 1 to 20. Each $R_9$ represents alkyl containing from 1 to 20 carbon atoms, aryl or hydrogen. If more than one $R_9$ is present, these may be the same or different. The valence of the group represented by Z (indicated by "a") is from 1 to 4. $R_{21}$ and $R_{22}$ are individually selected from the group consisting of alkyl, hydroxyalkyl, aryl, aralkyl and cycloalkyl wherein any alkyl residues contain from 1 to 20 carbon atoms, —SR, —OR (wherein R is hydrocarbyl), $$\text{acetoxy}\left(\begin{array}{c}O\\ \|\\ CH_3CO\end{array}\right),$$

halogen (chlorine, bromine or iodine), and —OH. $R_{23}$ represents —ORO—, —SRS— or —SRO—, wherein R is alkylene containing from 1 to 20 carbon atoms, —CH$_2$CH=CHCH$_2$—, —CH$_2$C≡CCH$_2$—, or arylene, most preferably phenylene. $R_{24}$ is —OR wherein R is hydrocarbyl (as previously defined) or —SnR$_{13}$R$_{14}$R$_{15}$. $R_{25}$ and $R_{26}$ are individually selected from hydroxyl, acyloxy, $$\begin{array}{c}|\\ CH_3COCHCOCH_3,\end{array}$$

pyrophosphate, halogen (chlorine, bromine or iodine), —OR', —OOCR', —OSi(R')$_3$, $$\begin{array}{ccc}O & S & S\\ \|\ & \|\ & \|\\ -OP(R')_2, & -OP(R')_2\text{ or } & -SP(R')_2\end{array}$$

wherein R' is hydrocarbyl as previously defined for R, SR", wherein R" is hydrocarbyl, or —R'''COOR" wherein R''' is alkylene containing from 2 to 20 carbon atoms that is optionally substituted with one or more halogen atoms or hydroxyl groups. $R_{27}$ is hydrocarbyl containing from 1 to 10 carbon atoms, —OOCR"" or —OR"" wherein R"" is hydrocarbyl, $$\begin{array}{c}R_4\diagdown\ \diagup^{A_c-Sn-}\\ \diagup\ \diagdown\\ R_1SnSR_2O-\end{array}\text{ or }\begin{array}{c}A\\ \|\\ R_1SnSR_2O-\end{array}$$

wherein $R_1$, $R_2$, $R_4$ and $A_c$ are previously defined in the general formulae for the present compounds; $R_{28}$ is hydrocarbyl; $R_{29}$ is hydrocarbyl, halogen (chlorine, bromine or iodine), —SR$_{10}$COOR$_{11}$ (R$_{10}$ and R$_{11}$ are as previously defined), or —SR$_{38}$OOCR$_{39}$, wherein $R_{38}$ is alkylene containing from two to twenty carbon atoms and $R_{39}$ is hydrocarbyl as previously defined or is —OR$_{28}$.

$R_{30}$ is —ORO—, —SRO— or —SRS— (R is alkylene containing from 2 to 8 carbon atoms), —OCH$_2$CH=CHCH$_2$O, —OCH$_2$—C≡C—CH$_2$O— or —OArO— wherein Ar is arylene, most preferably phenylene. $R_{31}$ is hydrocarbyl as previously defined for $R_1$. $R_{32}$ is alkyl containing from 1 to 20 carbon atoms or both $R_{32}$ groups are joined to form a single alkylene or alkenylene group containing from 2 to 10 carbon atoms, hydroxyl, nitro or halogen (chlorine, bromine or iodine), $M_1$ is an element having a valence equal to g and selected from the group consisting of aluminum, boron, phosphorus, silicon and titanium. Alternatively $M_1$ represents a residue of a compound of aluminum, boron, phosphorus, silicon or titanium. The compound contains at least one group bonded to said element that can displace the hydrogen atom of a hydroxyl group that is bonded to a carbon atom. $M_2$ represents an element selected from groups I$_A$, II$_A$ and II$_B$ of the periodic table of the elements and having a valence of m. $R_{34}$ and $R_{36}$ are individually selected from the group consisting of hydrogen, hydroxyl, —OR$_3$ and alkyl containing from 1 to 8 carbon atoms. $R_{35}$ and $R_{37}$ are individually selected from the group consisting of hydrogen and alkyl containing from 1 to 18 carbon atoms.

When one or more of $R_1$, $R_3$, $R_4$, $R_{13}$, $R_{14}$, $R_{15}$, $R_{35}$ and $R_{36}$ are hydrocarbyl they can be, for example, methyl, ethyl, propyl, isopropyl, n-butyl, isobutyl, sec-butyl, t-butyl, amyl, isoamyl, n-octyl, isooctyl, 2-ethylhexyl, dodecyl, benzyl, phenyl, p-tolyl, allyl, octadecyl, vinyl, oleyl, cyclopentyl or cyclohexyl. When one or more of these hydrocarbyl groups are substituted, they can be, for example, 3-ketopentyl, 4-ketopentyl, 4-ketoheptyl, β-carboethoxyethyl, β-carbotetrahydrofurfuryloxyethyl or β-carbo-2, 2'-dimethylolbutoxyethyl.

When $R_1$ and $R_3$ represent unsubstituted hydrocarbyl, these are preferably methyl, n-butyl or n-octyl. Preferred substituted hydrocarbyls represented by $R_1$ and $R_3$ include β-carboethoxyethyl, β-carbotetrahydrofurfuryloxyethyl and 4-ketopentyl.

The mercaptoalkanolic moiety attached to the tin through sulfur can be mercaptoalkanol or mercaptohydroxyalkanol containing at least 2 carbon atoms and usually not over 6 carbon atoms. Preferably, it contains 2 or 3 carbon atoms and only 1 hydroxyl group. The most preferred compounds include mercaptoethanol and mercaptopropanol, however, mercaptoalkanols containing 2 or more hydroxyl groups such as monothioglycerol and monothiopentaerythritol are also useful, as are esters thereof such as bis(monothioglycerol)succinate, the bis(monothioglycerol) ester of Empol® 1010 dimer acid, a hexatriocontanedioic acid available from Emery Industries, bis(monothioglycerol) dithiodipropionate, bis(monothiopentaerythritol) thiodiacetate and the bis(monothiopentaerythritol)ester of Westvaco Diacid 1500 (available from Westvaco Chemicals Company).

Alternatively, the mercaptoalkanolic moiety can be an ether, thioether, a poly(alkylene oxide) condensate, or a bis-, tri- or polymercaptoalkyl ester of a di-, tri- or polybasic carboxylic acid, such as bis(2-mercaptoethyl) oxalate, bis(2-mercaptoethyl) malonate, bis(3-mercaptopropyl) succinate, bis(2-mercaptoethyl) glutarate, bis(2-mercaptoethyl) adipate, bis(2-mercaptoethyl)azelate, the bis(3-mercaptopropyl) diester of Empol® 1010 dimer acid, bis(3-thioglyceryl) pimelate, the bis(2-mercaptoethyl) ester of Gulf PA-18 dicarboxylic acid, bis(7-mercaptoheptyl) dodecenyl succinate, bis(2-mercaptoethyl) phthalate, the tris(2-mercaptoethyl)ester of Empol® 1041 trimer acid, the mixed bis(2-mercaptoethyl)butyl ester of Empol® 1056A poly-basic acid, bis(3-mercaptoheptyl)maleate, the bis(2-mercaptoethyl) ester of Westvaco Diacid 1550 dicarboxylic acid, bis(2-mercaptoethyl) dithiodipropionate, bis(2-mercaptoethyl) maleate and bis(2-mercaptoethyl) thiomalate. Gulf PA-18 is a dicarboxylic acid anhydride available from Gulf Oil Chemical Corporation.

In addition to containing (1) a sulfur atom bonded solely to tin or to tin and hydrogen, a polysulfide group attached solely to tin or an oxygen atom bonded solely to tin or to tin and hydrogen and (2) at least one mercaptoalkanol group bonded to tin through sulfur and through oxygen to hydrogen, phosphorus, silicon, boron, aluminum, titanium or to a polycarboxylic acid wherein at least two carboxyl groups are esterified with one or more different mercaptoalkanols, the tin atom or atoms of the present compound can be bonded directly to a halogen or pseudo-halogen or through an oxygen or sulfur atom to substituents such as the residues of mercaptoacid esters, including isooctyl mercaptoacetate, aliphatic and aromatic mercaptans such as lauryl mercaptan, thiophenol and benzylmercaptan, monocarboxylic and polycarboxylic acids and partial esters of polycarboxylic acids, particularly those esters wherein the esterifying alcohol is a mercaptoalkanol wherein the sulfur atom is bonded to a tin atom.

The compounds of this invention are particularly useful as stabilizers for poly(vinyl chloride) homopolymers and copolymers and can be employed for this purpose as relatively pure monoorganotin or diorganotin compounds, physical mixtures of individual monoorganotin compounds with individual diorganotin compounds or as compounds containing both monoorganotin and diorganotin groups. Examples of each of these classes of compounds are contained in this specification. As used herein the term "relatively pure" means a concentration of at least 90% by weight of a mono- or diorganotin reactant in the starting materials employed to prepare the desired product, e.g., 90+% pure monooctyltin trichloride. The other 10% is usually the corresponding monoorganotin trichloride or diorganotin dichlorid respectively. In those instances when it is desirable to have a triorganotin species in the molecule, it too may be derived from a relatively pure triorganotin reactant such as 90+% pure tributyltin chloride containing 10% of a mixture of dibutyltin dichloride and monobutyltin trichloride. In place of the halides one can employ organostannoic acids, diorganotin oxides and/or triorganotin oxides of equivalent purity. The term "mixtures" is defined as physical blends of relatively pure monoorganotin compounds, diorganotin compounds and, optionally, triorganotin compounds, particularly mixtures having from 50 to 96% by weight of at least one monoorganotin compound and, correspondingly, from 4 to 50% of at least one diorganotin compound. These definitions differentiate a mixture of monoorganotin compound and a diorganotin compound from mixed mono-diorganotin compounds wherein two or more tin atoms are chemically bonded in the same molecule. The bonding is through sulfide or polysulfide groups, oxide groups, residues of dicarboxylic acids, mono-esters of tri-basic acids or di(mercaptoalkyl)ethers.

In the foregoing definition for Z some of the groups contain more than one unfilled valence. An example of such a

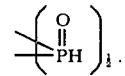

It will be understood that the remaining valence bonds are to

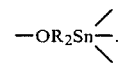

This can be the same tin atom that the Z group is bonded to. The resultant molecule would then exhibit the structure

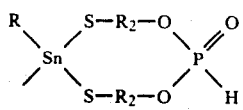

Alternatively, the phosphorus or other atom can be bonded to two different tin atoms through mercaptoalkanol residues.

preferably Z represents

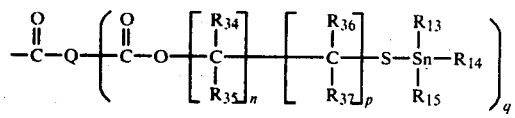

wherein Q is a bond between two carbonyl groups or a di- or polyvalent hydrocarbon residue such as $(CH_2)_r$ (r being defined as an integer from 1 to 18), an unsaturated hydrocarbon group such as —CH=CH—,

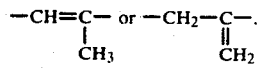

Alternatively, Q can represent two alkylene groups separated by from 1 to 4 sulfur atoms or it can represent residue of a di-, tri-, or polybasic acid such as are commercially produced by polymerization of unsaturated fatty acids. These products contain from 36 to 72 or more carbon atoms and are exemplified by Empol® 1010 dimer acid, Empol® 1012 dimer acid, Empol® 1014 dimer acid, Empol® 1016 dimer acid, Empol® 1018 dimer acid, Empol® 1022 dimer acid, Empol® 1024 dimer acid, Empol® 1040 trimer acid and Empol® 1041 trimer acid, Empol® 1056A polybasic acid, Hystrene® 3695 dimer acid (available from Humko Sheffield Chemicals, Inc.), Hystrene® 3680 dimer acid, Hystrene® 3675 dimer acid or Hystrene 5460 trimer acid. Q may also represent the residue of a 21 carbon atom diacid,

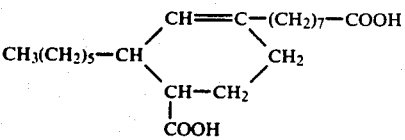

the residue of dodecenylsuccinic anhydride, one of several isomers of which is

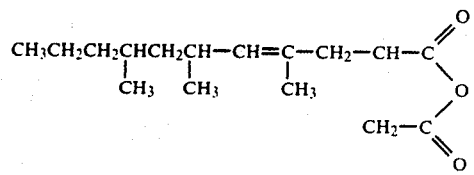

the residue of a low molecular weight polyanhydride resin wherein the repeating unit is

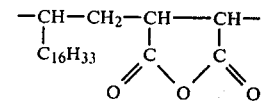

the residue of polyazelaic polyanhydride, the residue of phthalic acid, isophthalic acid, terephthalic acid or other benzenepolycarboxylic acids, the residue of malonic acid, succinic acid, glutaric acid, adipic acid, pimelic acid, cyclohexane dicarboxylic acid, or cyclohexane tetracarboxylic di-anhydride; the residues of certain diels-alder reaction products such as the cyclopentadiene-maleic anhydride adduct, 4-endomethylenetetrahydrophthalic anhydride, the furan-maleic anhydride adduct,

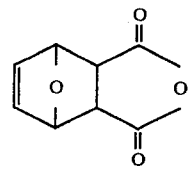

linoleic acid-maleic anhydride adduct, rosin acids-maleic anhydride adducts, alloocimene-maleic anhydride adduct, chlorendic anhydride and related products and derivatives. In those instances where Q is the residue of a tribasic carboxylic acid, one of the acid groups can exist as a substituted or unsubstituted aliphatic ester derivative; when the carboxylic acid represented by Q has a functionality of 4 or more, two or more acid groups can exist as substituted or unsubstituted aliphatic esters so long as two of the available valences of Q are satisfied by

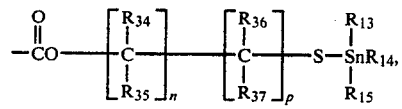

wherein $R_{34}$, $R_{35}$, $R_{36}$ and $R_{37}$ are as defined above, $R_{13}$, $R_{14}$ and $R_{15}$ can be as described for $R_1$ and $R_4$, however, it is optional, but not preferable that $R_{13}$, $R_{14}$ and $R_{15}$ are all hydrocarbyl since stabilization efficacy may decrease and toxicity may increase for these compounds. Preferably 1 or 2 groups selected from $R_{13}$, $R_{14}$ and $R_{15}$ are hydrocarbyl and most preferably one of $R_{13}$, $R_{14}$ and $R_{15}$ is identical to $R_1$; n and p are each integers of from 1 to 20 and r is an integer having a value of q−1, where q is the valence of Q. If two or more "Q" groups are present, these may be identical or different.

In addition to the groups of compounds described in the foregoing specification, there can also be employed "over-based" organotin compounds obtained by reacting any of the previously disclosed compounds containing a

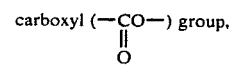

with monomeric or polymeric compounds of the formula:

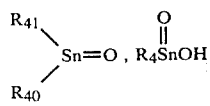

or $(R_{40}SnO_{1.5})_4$ where $R_{40}$ and $R_{41}$ are hydrocarbyl or substituted hydrocarbyl as defined for $R_1$ in the general formulae for the present compounds. These compounds are used in an amount of up to 3 moles per mole of available carboxyl groups within the organotin molecules of this invention. The over-based product can be obtained simply by dissolving the diorganotin oxide, organostannoic acid or an anhydride of said acid in the compound of this invention having either mercaptoalkanol ester functionality or mercaptoacid ester functionality. Only a fraction of the stoichiometric amount of an organotin oxide or organostannoic acid will dissolve in a mercaptoacetate derivative, e.g., up to 0.3 mole of oxide or acid per mole mercaptoacetate. Surprisingly, mercaptopropionates are not similarly restricted.

Over-basing reactions of organotin compounds are disclosed by Weisfeld (U.S. Pat. No. 3,478,071), and by Stapfer and Dworkin, et. al. J. Organometallic Chemistry-Volume 24 (1970) Pages 355–358. The relevant portions of the Weisfeld patent are hereby incorporated by reference.

As employed in the present specification and claims, the term "over-based" is defined as the reaction product of a diorganotin oxide or organostannoic acid with any organotin compound containing a residue of a mono- or polycarboxylic acid or a mercaptoacid ester. While not being limited to any theory, it is believed that the over-basing reactions proceed in one or more of the following ways:

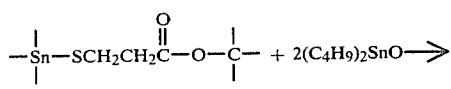

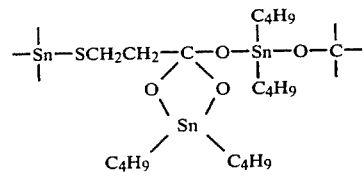

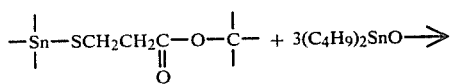

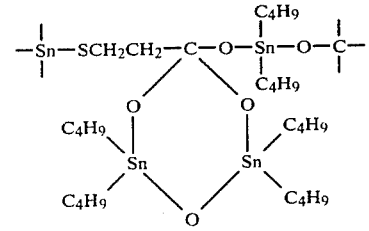

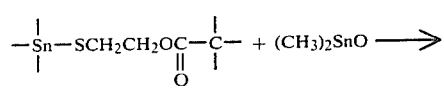

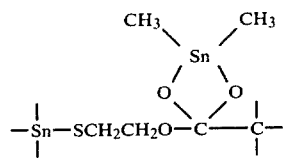

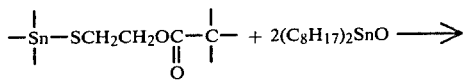

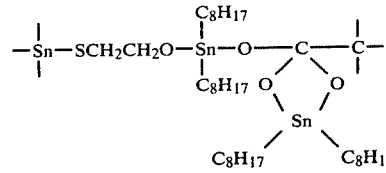

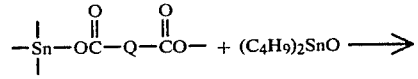

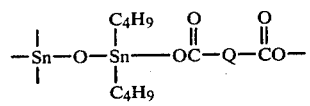

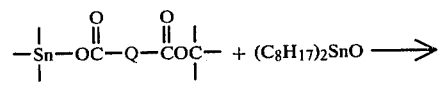

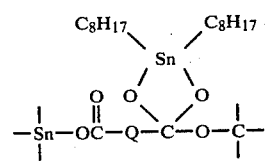

When over-basing is employed $R_4$ is further defined as:

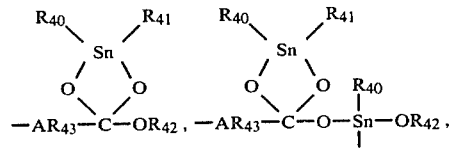

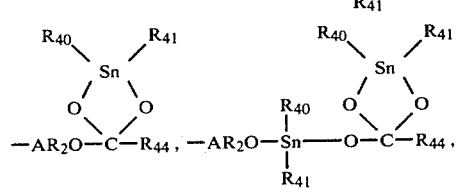

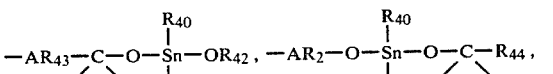

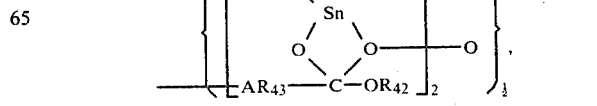

-continued

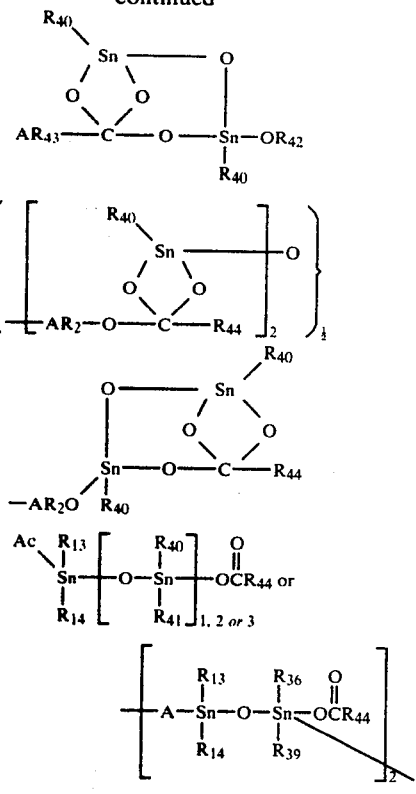

wherein $R_{40}$ and $R_{41}$ are as defined hereinbefore, $R_{42}$ is alkyl, alkaryl, cycloalkyl, alkenyl, of 1 to 20 carbon atoms, or functionally substituted derivatives thereof, e.g., hydroxyalkyl, alkoxyalkyl, alkyl aryl ether, alkylthio ether, alkyl polythio ether, or a phosphite, borate, silicate, aluminate or titanate derived from a hydroxyl-terminated alkyl group, for example, $-CH_2CH_2O(\!-\!P)_{\frac{1}{3}}$, $-CH_2CH_2OCH_2CH_2OP(OC_2H_5)_2$, $-CH_2CH_2-S-CH_2CH_2O(Si)_{\frac{1}{4}}$, $-CH_2CH_2SSSCH_2CH_2O(\!-\!Si(C_6H_5)_2]_{\frac{1}{2}}$.

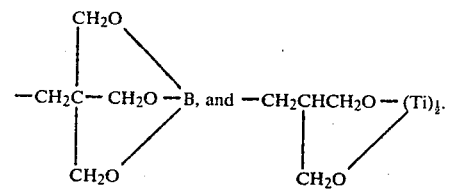

$R_{43}$ is a polyvalent alkylene residue of an $\alpha$-, $\beta$- or $\gamma$-mercaptoacid or an ester thereof, for example $-CH_2-$, $-CH_2CH_2-$, $-CH_2CH_2CH_2-$, $$-\underset{\underset{CH_3}{|}}{CH}-CH_2- \text{ and } -CH_2\underset{\underset{CH_3}{|}}{CH}CH_2-.$$

$R_{44}$ is defined as,

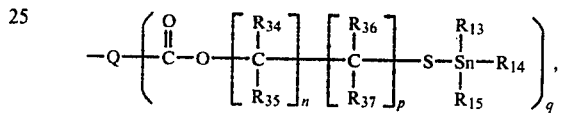

the component terms of which are as previously defined.

The following structural formulae are representative of typical compounds of this invention and are not meant to limit the scope of the invention as defined in this specification and the accompanying claims. The roman numerals above and to the left of each formula identifies the generic formula to which the compound corresponds.

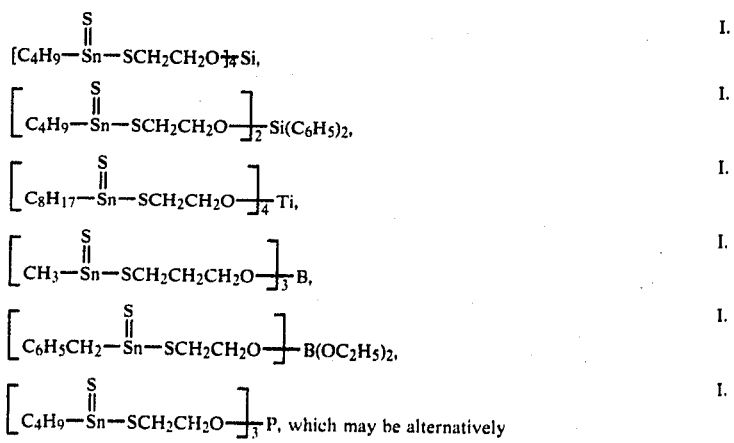

-continued
written as
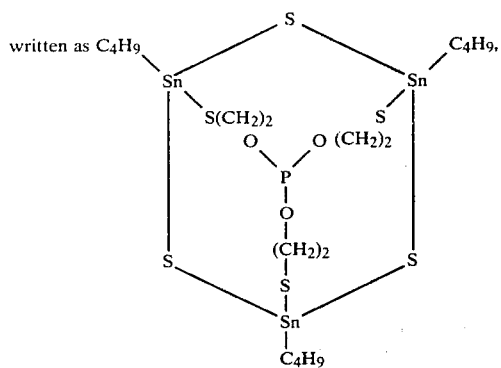
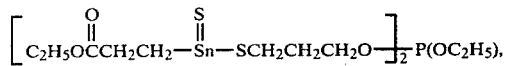     I.
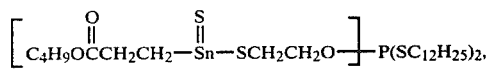     I.
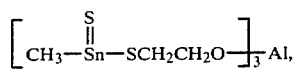     I.
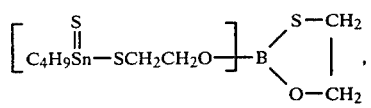     I.
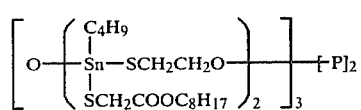     II.
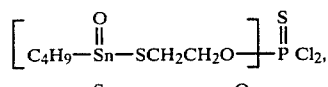     I.
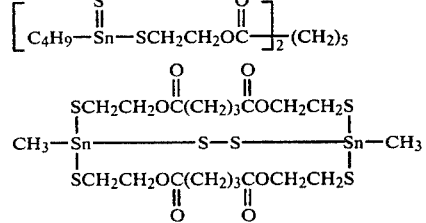     I.
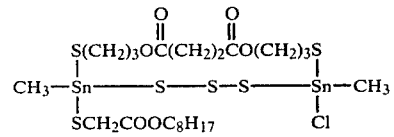     III.
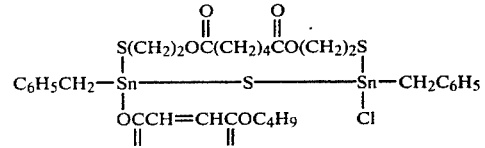    III.
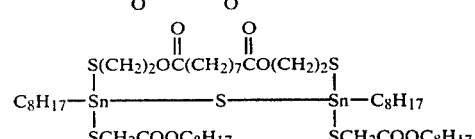    III.
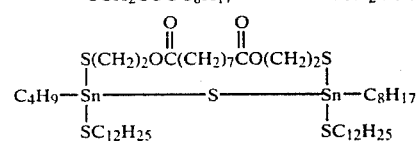    III.
III.

-continued
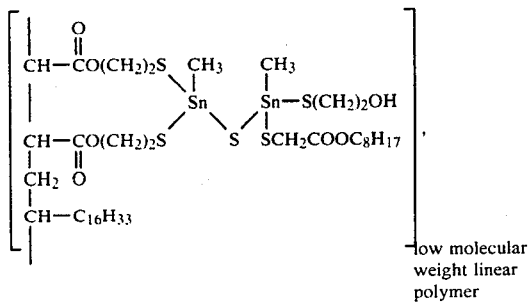 IIIA.
low molecular weight linear polymer
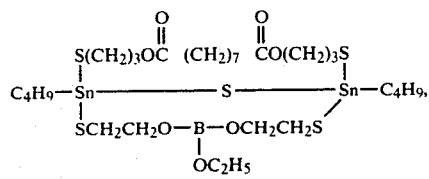 III.
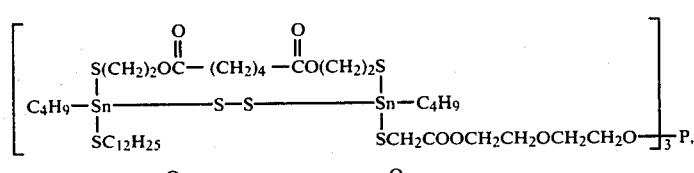 II.
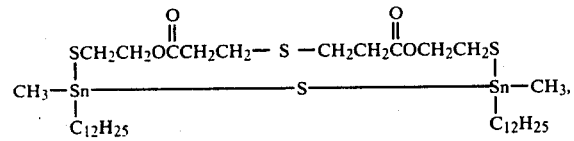 III.
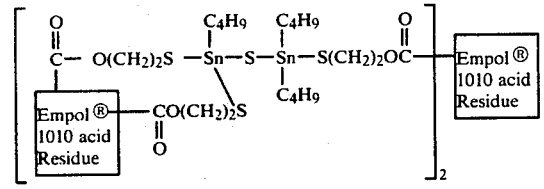 IIIA.
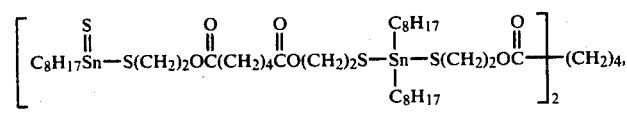 IA.
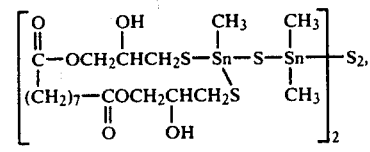 IIIB.
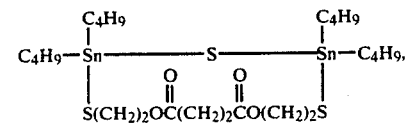 III.
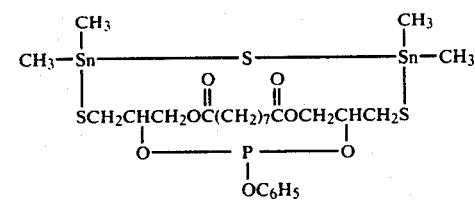 III.
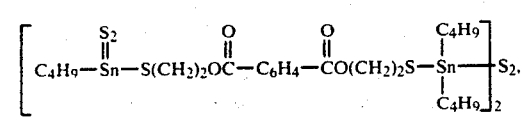 I.

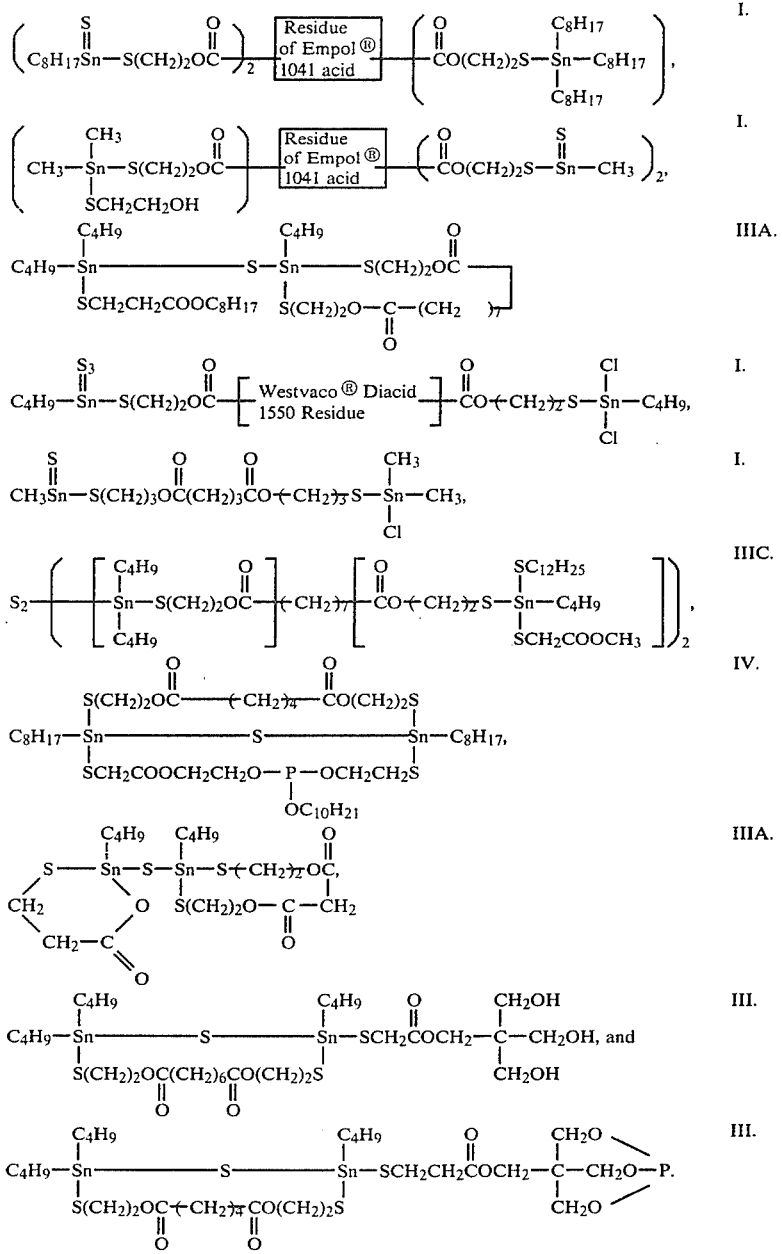

The compounds of the present invention can be prepared using a variety of known synthetic methods, some of which are exemplified hereinafter. Thus, for example, there can be used the procedure of Kauder, U.S. Pat. No. 3,565,930, or Brecker, U.S. Pat. No. 3,565,931 substituting alkali metal, alkaline earth metal or ammonium sulfides or polysulfides for the alkali metal or alkaline earth metal mono-sulfide of Kauder or Brecker and also substituting for the isooctylthioglycolate or other mercaptoacid ester of Brecker and Kauder a compound and the formula $HSR_2(OH)_s$ wherein $R_2$ is as previously defined and s is 1, 2 or 3. For the preferred compounds of this invention s is 1 and the mercaptoalkanol exhibits the general formula

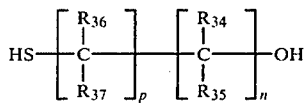

wherein $R_{34}$, $R_{35}$, $R_{36}$ and $R_{37}$ are previously defined. Alternatively the mercaptoalkanol is reacted with a compound of the formula ZX wherein X represents an active hydrogen atom of the carboxylic acid or any other atom such as halogen or an alkali metal which reacts with alcohols to form an —OZ bond.

The mercaptoalkanol or a derivative thereof containing a free mercapto (HS—) group is reacted with a stoichiometric amount of a mono- or diorganotin halide, a diorganotin oxide or an organostannoic acid. It will be understood that the relative amounts of organotin compound and mercaptoalkanol employed will depend upon the molar ratio of tin to mercaptoalkanol residues in the desired compound. For example, if an organotin trichloride such as butyltin trichloride is reacted with mercaptoethanol or a suitable derivative thereof, ammonia and an alkali metal sulfide to yield a product of the formula

equimolar amounts of the four reagents would be employed. The aforementioned esters of polycarboxylic acids and mercaptoalkanols can be formed during the reaction of the organotin compound with the mercaptoalkanol by including in the reaction mixture the required amount of mercaptoalkanol and the polycarboxylic acid or an ester thereof derived from a low boiling alcohol such as methanol.

If the organotin compound employed for the reaction with the mercaptoalkanol is a halide, the reaction mixture is neutralized using an alkali metal- or alkaline earth metal hydroxide or ammonium hydroxide in an amount sufficient to react with the hydrogen halide formed as a by-product of the aforementioned reaction.

Suitable organotin halides include methyltin trichloride, methyltin tribromide, methyltin triiodide, ethyltin trichloride, butyltin trichloride, butyltin tribromide, butyltin triiodide, sec-butyltin trichloride, octyltin trichloride, benzyltin trichloride, dimethyltin dichloride, dimethyltin dibromide, dimethyltin diiodide, dipropyltin dichloride, butyl methyltin dichloride, dibutyltin dichloride, dibutyltin dibromide, dioctyltin diiodide, dioctyltin dichloride, dibenzyltin dichloride, phenyltin trichloride, p-tolytin trichloride, diphenyltin dichloride, di-p-tolytin dichloride, cyclohexyltin trichloride, dicyclohexyltin dichloride, cyclopentyltin trichloride, oleyltin trichloride, dioleytin dichloride, vinyltin trichloride, diallyltin dichloride, allyltin trichloride, eicosanyltin trichloride, n-dodecyltin trichloride, di(n-dodecyl)-tin dichloride, di($\beta$-carboethoxyethyl)tin dichloride, $\beta$-carboethoxyethyltin trichloride, di(4-ketopentyl) tin dichloride, 4-ketopentyltin trichloride, diisobutyltin dichloride, isobutyltin trichloride, tri-n-butyltin chloride and tri-n-octyltin chloride.

As the bis-, tris or poly-mercaptoalkanol ester there can be employed, for example, a di-, tri-, or polycarboxylic acid ester of mercaptoethanol, 2-thioglycerine, 3-thioglycerine, 3-thiopropanol, 2-thiopropanol, 4-thiobutanol, 18-thiooctadecanol, 9-thiononanol, 8-thiooctanol or 6-thiohexanol. Suitable polyfunctional carboxylic acids include oxalic, malonic, succinic, dodecenylsuccinic, glutaric, adipic, benzylmalonic, bromosuccinic, citric, tartaric, gluconic, glyceric, methyl succinic, methyl malonic, $\beta$-methyltricarballylic, mucic, phenylmalonic, p-phenylenedipropionic, o-, m- and p-phenylene diacetic, tricarballylic, tropic, pimelic, suberic, azelaic, sebacic, undecanedioic, dodecanedioic, maleic, fumaric, itaconic, glutaconic, citraconic, mesaconic, bromomaleic, traumatic, aconitic, malic, trans-, trans-muconic, 2-ketoglutaric, 1,3-acetonedicarboxylic, 4-ketopimelic, 1,1-cyclohexanediacetic, cyclohexanedicarboxylic, cyclohexanetetracarboxylic, benzylmalonic, diglycolic, thiodiglycolic, dithiodiglycolic, thiodipropionic, dithiodipropionic, phthalic, isophthalic and terephthalic acids. Other suitable polycarboxylic acids include Westvaco ® Diacid 1550, Empol ® 1010 Dimer Acid, thiomalic acid, Empol ® 1012 Dimer Acid, Empol ® 1014 Dimer Acid, Empol ® 1016 Dimer Acid, Empol ® 1018 Dimer Acid, Empol ® 1022 Dimer Acid, Empol ® 1024 Dimer Acid, Empol ® 1040 Trimer Acid, Empol ® 1041 Trimer Acid, Empol ® 1056A Poly-basic Acid, Diels-Alder adducts of maleic anhydride and dienes such as cyclobutadiene, hexachlorocyclopentadiene, furan, linoleic acid and the various rosin acids.

Illustrative of the mercaptoalkanol esters of polycarboxylic acids that can be reacted with organotin halides, oxides or organostannoic acids are:
Bis(2-mercaptoethyl) oxalate,
Bis(2-mercaptoethyl) malonate,
Bis(2-mercaptoethyl) succinate,
Bis(2-mercaptoethyl) glutarate,
Bis(2-mercaptoethyl) adipate,
Bis(2-mercaptoethyl) citrate,
Bis(2-mercaptoethyl) methylmalonate,
Bis(2-mercaptoethyl) pimelate,
Bis(2-mercaptoethyl) suberate,
Bis(2-mercaptoethyl) azelate,
Bis(2-mercaptoethyl) sebacate,
Bis(2-mercaptoethyl) dodecanoate,
Bis(2-mercaptoethyl) maleate,
Bis(2-mercaptoethyl) itaconate,
Bis(2-mercaptoethyl) citraconate,
Bis(2-mercaptoethyl) traumatate,
Bis(2-mercaptoethyl) malate,
Bis(2-mercaptoethyl) aconitate,
Bis(2-mercaptoethyl) 2-ketoglutarate,
Bis(2-mercaptoethyl) 4-ketopimelate,
Bis(2-mercaptoethyl) cyclohexanedicarboxylate,
Bis(2-mercaptoethyl) diglycolate,
Bis(2-mercaptoethyl) dithioglycolate,
Bis(2-mercaptoethyl) thiodiacetate,
Bis(2-mercaptoethyl) thiodipropionate,
Bis(2-mercaptoethyl) dithiodipropionate,
Bis(2-mercaptoethyl) phthalate,
Bis(3-mercaptopropyl) isophthalate,
Bis(3-thioglyceryl)terephthalate,
Bis(6-mercaptohexyl)Westvaco ® Diacid 1550 dicarboxylate,
Bis(2-thioglyceryl)Empol ® 1010 Dimer Acid dicarboxylate,
Bis(2-mercaptoethyl)Gulf ® PA-18 dicarboxylic polymer,
Bis(2-mercaptoethyl)thiomalate,
Bis(2-mercaptoethyl)Empol ® 1040 Trimer Acid dicarboxylate,
Tris(3-mercaptopropyl)Empol ® 1041 Trimer Acid tricarboxylate,
Bis(2-mercaptoethyl)Empol ® 1056A Poly-basic Acid dicarboxylate,
Tetra(7-mercaptoheptyl)cyclohexane tetracarboxylate.

As previously disclosed, the reaction mixture containing the organotin compound and the mercaptoalkanol or derivative thereof can include one or more additional reagents, depending upon the substituents desired in the final product. Among the class of suitable coreactants are esters of mercaptoacids, such as mercaptoacetic acid, alpha-mercaptopropionic acid, beta-mercaptopropionic acid, alpha-mercaptobutyric acid, beta-mercaptobutyric, gamma-mercaptobutyric acid, gamma-mercaptovaleric acid, alpha-mercaptovaleric acid, beta-mercaptovaleric acid and thiomalic acid; esters of mercaptocarboxylic acids, including methyl mercaptoacetate (methyl thioglycolate), ethyl mercaptoacetate, propyl mercaptoacetate, butyl mercaptoacetate, isobutyl mercaptoacetate, sec-butyl mercaptoacetate, t-butyl mercaptoacetate, amyl mercaptoacetate, hexyl mercaptoacetate, octyl mercaptoacetate, isooctyl mercaptoacetate, 2-ethylhexyl mercaptoacetate, decyl mercaptoacetate, isodecyl mercaptoacetate, lauryl mercaptoacetate, myristyl mercaptoacetate, hexadecyl mercaptoacetate, stearyl mercaptoacetate, allyl mercaptoacetate, methallyl mercaptoacetate, crotyl mercaptoacetate, oleyl mercaptoacetate, cyclopentyl mercaptoacetate, cyclohexyl mercaptoacetate, 2-methylcyclohexyl mercaptoacetate, benzyl mercaptoacetate, methyl beta-mercaptopropionate, ethyl beta-mercaptopropionate, isopropyl beta-mercaptopropionate, octyl beta-mercaptopropionate, nonyl beta-mercaptopropionate, isooctyl beta-mercaptopropionate, 2-ethylhexyl beta-mercaptopropionate, decyl beta-mercaptopropionate, octadecyl beta-mercaptopropionate, allyl beta-mercaptopropionate, oleyl beta-mercaptopropionate, benzyl beta-mercaptopropionate, cyclohexyl beta-mercaptopropionate, methyl alpha-mercaptopropionate, hexyl alpha-mercaptopropionate, nonyl alpha-mercaptopropionate, octyl alpha-mercaptopropionate, isooctyl alpha-mercaptopropionate, stearyl alpha-mercaptopropionate, oleyl alpha-mercaptopropionate, methyl alpha-mercaptobutyrate, octyl alpha-mercaptobutyrate, isooctyl alpha-mercaptobutyrate, octadecyl alpha-mercaptobutyrate, oleyl alpha-mercaptobutyrate, ethyl gamma-mercaptobutyrate, octyl gamma-mercaptobutyrate, 2-ethylhexyl gamma-mercaptobutyrate, isooctyl gamma-mercaptobutyrate, benzyl gamma-mercaptobutyrate, cyclopentyl gamma-mercaptobutyrate, oleyl gamma-mercaptobutyrate, isopropyl delta-mercaptovalerate, octyl delta-mercaptovalerate, isooctyl delta-mercaptovalerate, octadecyl delta-mercaptovalerate, oleyl delta-mercaptovalerate, cyclohexyl delta-mercaptovalerate, benzyl delta-mercaptovalerate, dimethylthiomalate, dibutylthiomalate, diisobutylthiomalate, di-sec-butylthiomalate, di-t-butylthiomalate, diamylthiomalate, dihexylthiomalate, di-n-octylthiomalate, diisooctylthiomalate, di-2-ethylhexylthiomalate, didecylthiomalate, diisodecylthiomalate, didodecylthiomalate, dihexadecylthiomalate, dioctadecylthiomalate, diallylthiomalate, dicyclopentylthiomalate, dicyclohexylthiomalate, dibenzylthiomalate and dioleylthiomalate. Another class of useful coreactants are mercaptans such as octyl mercaptan, dodecyl mercaptan, stearyl mercaptan, oleyl mercaptan, methoxyethyl mercaptan, ethoxyethyl mercaptan, octoxyethyl mercaptan, ethoxypropyl mercaptan, tridecyl mercaptan, tridecyl mercaptan, cyclohexyl mercaptan and thiophenol. The hydrocarbyl groups of the aforementioned mercaptans can be linear or branched. An example of the latter class of compounds is t-dodecyl mercaptan. Other suitable coreactants include thiocarboxylic acids such as thioacetic acid, thiolauric acid, thiobenzoic acid and thiostearic acid; substituted and unsubstituted monocarboxylic acids such as acetic acid, caprylic acid, stearic acid, heptanoic acid, elaidic acid, oleic acid, benzoic acid, isostearic acid, neo-pentanoic acid, hydroxystearic acid, chloroacetic acid and epoxy stearic acid; half esters of dicarboxylic acids such as allyl hydrogen maleate, methyl hydrogen maleate, butyl hydrogen maleate, isooctyl hydrogen maleate, butyl hydrogen glutarate, amyl hydrogen adipate, hexyl hydrogen pimelate, n-octyl hydrogen suberate, isooctyl hydrogen azelate, monobutyl citrate, monolauryl thiodipropionate, methyl hydrogen phthalate, the monoisooctyl ester of Empol ® 1010 acid, the dibutyl ester of Empol ® 1040 acid; dicarboxylic acids such as oxalic acid, malonic acid, succinic acid, glutaric acid, adipic acid, gluconic acid, citric acid, tropic acid, pimelic acid, suberic acid, azelaic acid, sebacic acid, maleic acid, 4-ketopimelic acid, fumaric acid, itaconic acid, malic acid, cyclohexane dicarboxylic acid, diglycolic acid, thiodipropionic acid, dithioglycolic acid and phthalic acid; anhydrides of carboxylic acids including meleic anhydride, phthalic anhydride, Westvaco ® Diacid 1550, Empol ® 1016 Dimer Acid, Empol ® 1040 Trimer Acid, Empol ® 1056A Poly-basic Acid, Hystrene ® 3680 Dimer Acid and 4-endomethylenetetrahydrophthalic acid.

Boron compounds that can be employed as reagents to prepare one class of compounds encompassed by the present invention include, but are not limited to boric acid, boric acid anhydride, trialkoxyboranes (or trialkylborates) such as trimethylborate, triethylborate, tributylborate, alkyleneborates such as:

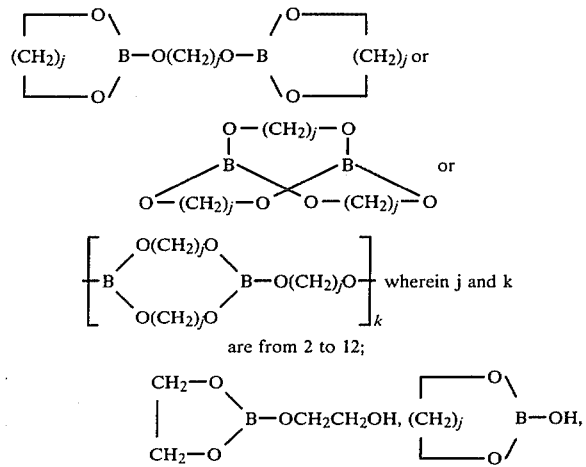

glycol borate, triethanolamine borate, halide derivatives such as $BF_3$, $BCl_3$, $CH_3BF_2$, $(CH_3)_2BF$, $C_6H_5BCl_2$, $(CH_3)_2O.BF_3$, $BBr_3$ and o-phenylene chloroboronate, $HBO_2$, o-nitrophenyl diethylborate, butyl dibromoborane, $C_6H_5B(OC_2H_5)_2$, $C_4H_9B(OH)_2$, $(C_4H_9)_2BOH$, $p-CH_3-C_6H_4-B(OH)_2$,

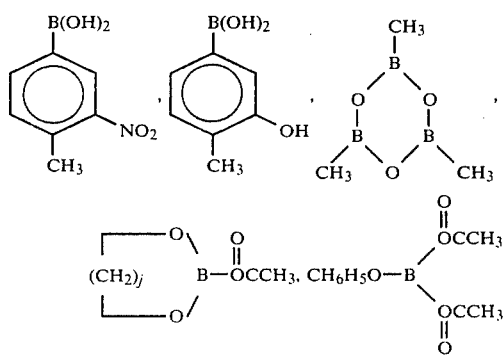

-continued

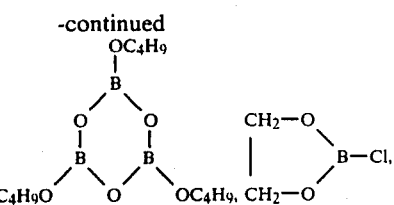

di-o-phenylenepyroborate, trialkylthioborates such as (C₄H₉S)₃B, (C₁₂H₂₅S)₃B, triarylthioborates like (C₆H₅S)₃B,

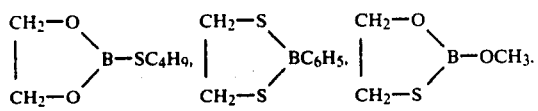

Aluminum compounds that can be used to prepare compounds of this invention include halides such as aluminum chloride, aluminum bromide, aluminum iodide, aluminum oxychloride, aluminum oxybromide; carboxylates such as aluminum acetate, Al(OH)(O₂CH₃)₂, aluminum propionate, Al(OH)₂(O₂CC₂H₅); alkoxides such as aluminum isopropoxide; aluminum hypophosphite, Al(H₂PO₂)₃; organoaluminums such as di-n-butyl(tetradecyl)aluminum, dimethylaluminumchloride, methylaluminumdichloride, di-n-butylaluminumisopropylate and diphenylaluminum-n-dodecylmercaptide.

Silicon compounds which are suitable for use in preparing compounds of this invention include, but are not limited to, silicon tetrachloride, tetraethylorthosilicate, silicon tetraacetate, methoxy silicon triacetate, dimethoxy silicon diacetate, trimethoxysiliconacetate, tetramethylorthosilicate, tribromosiliconhydride, diethoxysilicondichloride, trimethylsiliconchloride, tributylsiliconchloride, trioctylsiliconchloride, triphenylsiliconchloride, dimethylsilicondichloride, dibutylsilicondichloride, diphenylsilicondichloride, methylsilicontrichloride, octylsilicontrichloride, diphenylsilanediol, triphenylsilanol, aminopropyltriethoxysilane, mercaptoethyltriethoxysilane, methyldichlorosilane, phenyltriethoxysilane, and diphenyldimethoxysilane.

Among the phosphorus compounds suitable for synthesizing desired products of this invention are halides such as phosphorous trichloride, phosphorus tribromide, phosphorous pentachloride, phosphoryl chloride and thiophosphoryl chloride; phosphoric acid, phosphorous acid, phosphoric pentoxide, tetraphosphorous hexasulfide, phosphorous pentasulfide, trimethylphosphite, triethylphosphite, tripropylphosphite, tributylphosphite, trioctylphosphite, triphenyl phosphite, phenyldidecylphosphite, didecylphosphite, trisnonylphenylphosphite, trimethylphosphate, tributylphosphate and compounds represented by the formulae (CH₂H₅O)₂P(O)H, (C₄H₉S)₃P, (C₁₂H₂₅S)₃P and (C₆H₅S)₃P.

The compounds of this invention that contain titanium can be prepared using as the titanium-containing reagent a titanium tetrahalide such as titanium tetrachloride, a mixed titanium halide such as trichlorotitanium bromide, an alkoxide or aryloxide such as tetraethyl titanate, tetrabutyl titanate and tetraphenyl titanate in addition to the 1:1 (equimolar) adducts of a titanate with phenol, ammonia, amines, dioxane and acetone, dimethoxytitanium dichloride, diphenoxytitanium dichloride, tris(chlorotitanium tributoxide) and tetrakis(trimethylsiloxytitanium) Ti(OSi[CH₃]₃)₄.

The compounds of this invention that contain titanium can be prepared using as the titanium-containing reagent a titanium tetrahalide such as titanium tetrachloride, a mixed titanium halide such as trichlorotitanium bromide, an alkoxide or aryloxide such as tetraethyl titanate, tetrabutyl titanate and tetraphenyl titanate in addition to the 1:1 (equimolar) adducts of a titanate with phenol, ammonia, amines, dioxane and acetone, dimethoxytitanium dichloride, diphenoxytitanium dichloride, tris(chlorotitanium tributoxide) and tetrakis(trimethylsiloxytitanium) Ti(OSiCH₃)₄.

The compounds of this invention can be employed as heat stabilizers and as catalysts for cellular and non-cellular polyurethanes, esterification reactions and as curing catalysts for silicone resins.

The compounds of the present invention are particularly useful as heat stabilizers for halogen containing vinyl and vinylidene polymers, e.g., resins in which the halogen is attached directly to the carbon atoms. Preferably the polymer is a vinyl halide polymer, specifically a vinyl chloride polymer.

The vinyl chloride polymer is usually produced from vinyl chloride alone or a mixture of monomers containing at least 70 wt. % vinyl chloride, the remainder being one or more copolymerizable, ethylenically unsaturated monomers. When vinyl chloride copolymers are stabilized, at least 10% of the product should be vinyl chloride which has preferably been copolymerized with an ethylenically unsaturated compound.

As the chlorinated polymer there can be employed chlorinated polyethylene having 14 to 75%, e.g., 27% chloride by weight, chlorinated natural and synthetic rubber, rubber hydrochloride, chlorinated polystyrene, chlorinated polyvinyl chloride, polyvinyl chloride, polyvinylidene chloride, polyvinyl bromide, polyvinyl fluoride, copolymers of vinyl chloride with 1 to 90%, preferably 1 to 30% of a copolymerizable ethylenically unsaturated material such as vinyl acetate, vinyl butyrate, vinyl benzoate, vinylidene chloride, diethyl fumarate, diethyl maleate, other alkyl fumarates and maleates, acrylonitrile, chloroacrylonitrile, allylidene diacetate and chloroallylidene diacetate, styrene, trichloroethylene, vinyl esters such as vinyl ethyl ether, vinyl chloroethyl ether and vinyl phenyl ether, vinyl ketones such as vinyl methyl ketone and vinyl phenyl ketone, 1-fluoro-2-chloro-ethylene, vinyl propionate, methyl acrylate, 2-ethylhexyl acrylate, butyl acrylate and other alkyl acrylates, methyl methacrylate, ethyl methacrylate, butyl methacrylate, methyl alpha chloroacrylate and other alkyl acrylates and methacrylates. Typical copolymer products include vinyl chloride-vinyl acetate, vinyl chloride-vinyl acetatemaleic anhydride, vinyl chloride-vinylidene chloride, vinyl chloride-diethyl fumarate, vinyl chloride-trichloroethylene and vinyl chloride-2-ethylhexyl acrylate. The foregoing copolymers contain from 50 to about 95% by weight of repeating units derived from vinyl chloride.

The stabilizers of the present invention can be incorporated into the halogenated polymer composition by combining the ingredients in an appropriate mill, mixer or any other apparatus which will yield a homogeneous polymer composition. A preferred method involves the use of a two-roll mill wherein the rollers of the mill are heated to between 100° and 160° C.

In addition to the novel stabilizers of this invention, the polymer composition optionally contains conventional additives such as fillers, pigments, lubricants, dyes, ultraviolet light absorbing agents, plasticizers, densifying agents and the like. In addition to one or more of the present compounds, a polymer composition may contain conventional organotin stabilizers such as those disclosed in the aforementioned Kauder or Kugele et al. patents or in Weisfeld, U.S. Pat. No. 3,640,950; Leistner, U.S. Pat. Nos. 2,870,119 and 2,870,182; Best, U.S. Pat. No. 2,731,484; Stefl, U.S. Pat. No. 2,731,482; and Mack, U.S. Pat. No. 2,914,506. Relevant portions of the disclosures of all the patents mentioned in this paragraph are hereby incorporated by reference. Other known organotin stabilizers such as monoorganotin tris(mercaptoalkyl)alkanoates, diorganotin bis(mercaptoalkanyl)alkanoates, mono- and/or diorganotin mercaptoacid esters, mono- and/or diorganotin mercaptoacid ester (poly)sulfides, organothiostannoic acids, diorganotin sulfides and mono- and/or diorganotin sulfide chlorides are also useful. Auxiliary stabilizers are not within the scope of this invention, however, their use in combination with the compounds of this invention is considered within the scope of this invention.

The tin-containing stabilizers of the invention are normally used in an amount of from 0.01 to 10% by weight of the polymer, preferably from 0.1 to 5% by weight.

There can also be incorporated 0.1 to 10 parts per 100 parts of the halogen containing polymer of a metal salt stabilizer, typical products being strontium, calcium, cadmium, zinc, lead, tin, barium, magnesium, cobalt, nickel, antimony and aluminum salts of phenols, aromatic carboxylic acids, fatty acids or epoxidized fatty acids, mercaptans and mercaptoesters.

Specific examples of useful metal salt stabilizers include barium di(nonylphenolate), strontium di(octylphenolate), strontium di(octylphenolate), barium di(nonyl-o-cresolate), barium laurate, barium ricinoleate, lead stearate, aluminum stearate, magnesium stearate, calcium octoate, lead di(octylphenolate), cadmium-2-ethylhexoate, cadmium laurate, cadmium stearate, zinc caprylate, cadmium caprate, barium stearate, barium-2-ethylhexoate, calcium stearate, cadmium naphthenate, cadmium benzoate, cadmium p-tert-butylbenzoate, barium octylsalicylate, cadmium epoxystearate, strontium epoxystearate, the cadmium salt of epoxidized acids of soybean oil, lead epoxystearate, barium myristate, calcium myristate, cadmium myristate, zinc myristate and zinc maleate.

When plasticizers are employed in the present polymer composition they are used at conventional levels, e.g., 5 to 150 parts per 100 parts of resin. Useful plasticizers include di-2-ethylhexyl phthalate, dioctyl adipate, di-butyl sebacate, tricresylphosphate, epoxidized soybean oils, diisononyl phthalate, tetra-ethylene glycol-di-2-ethylhexoate and tetrahydrofurfuryl oleate.

The stabilizers of this invention may also be used in plastisol formulations containing from 0.1 to 10 parts per 100 parts of halogen containing polymer of epoxidized vegetable oils such as epoxidized soybean oil, epoxidized tall oil or epoxidized fatty acid esters such as butyl epoxystearate and isooctyl epoxystearate.

The compounds of this invention can be prepared using one or more of the following procedures. Regardless of the method employed, the reactions can be carried out within a wide range of temperatures, i.e., from ambient temperature to 150° C. Preferably the reactions are conducted at from 25° to about 95° C. in an aqueous medium, regardless of the specific procedure employed. To facilitate separation of the desired product there can also be employed water-immiscible organic solvents such as aliphatic and aromatic hydrocarbons, e.g., hexane, octane, benzene, toluene, xylene, aliphatic carboxylic acid esters, e.g., butyl acetate, propyl propionate, and methyl valerate. The relative amounts of water and water-immiscible solvent are not critical and can vary widely.

PROCEDURE 1

The general procedure of Kauder and Brecker described in U.S. Pat. Nos. 3,565,930 and 3,565,931 is followed except that sodium monosulfide, sodium disulfide, sodium trisulfide, sodium tetrasulfide, ammonium monosulfide, ammonium disulfide, ammonium trisulfide or ammonium tetrasulfide is reacted with the appropriate tin compound and the mercaptoalkanol in addition to one or more of the optional classes of reagents listed hereinbefore.

PROCEDURE 2

Sodium mono- or polysulfide (or potassium mono- or polysulfide), water, mercaptoalkanol ester, optionally additional mercapto compounds, hydrocarbon (if desired) and ammonium hydroxide are charged into a reactor and an aqueous solution of an alkyltin halide is then slowly added to maintain the temperature of the reaction mixture at between 25° and about 65° C. The mixture is then heated, e.g., to 70° C., the aqueous and organic layers separated, and the product is washed, dried and, if necessary, filtered.

PROCEDURE 3

The mercaptoalkanol ester, optionally additional mercapto compound, water, organic solvent and ammonium hydroxide are changed into a flask. Two solutions containing (1) an alkyltin chloride and (2) an alkali metal mono- or polysulfide are then added simultaneously to the reactor. The product is then separated, washed and solvent is removed.

PROCEDURE 4

This is essentially the same procedure as Procedure 3 except that sodium bicarbonate is substituted in the same molar amount for the ammonium hydroxide.

PROCEDURE 5

The organotin chloride, water and ammonium hydroxide are charged into a flask. The mercaptoalkanol ester and alkali metal mono- or polysulfide are then added to the reactor simultaneously.

PROCEDURE 6

A reactor is charged with the mercaptoalkanol ester, water and ammonium hydroxide. An organotin chloride is then added, followed by the gradual addition of an alkali metal polysulfide or monosulfide to maintain the temperature of the reaction mixture from 30° to 60° C. After heating to 65° C. the product is separated, washed, solvent is removed and the product is filtered, if necessary.

PROCEDURE 7

A mercaptoalkanol is added to a partially neutralized organotin halide (the amount of base employed is less than that required to remove or neutralize all the halogen atoms on the organotin halide in an aqueous medium). The resultant hydroxy-terminated mercaptoalkanol derivative is then reacted with an alkali metal polysulfide or monosulfide at a temperature from 25° to 75° C. The reaction mixture is then heated at from 45° to 75° C. A di-, tri- or poly-basic acid, anhydride or a partial ester is then added, the aqueous phase of the reaction mixture is removed and the hydroxyl group of the mercaptoalkanol residue is esterified or transesterified by reacting it with a polycarboxylic acid or an ester thereof under an inert atmosphere. The by-product water or alcohol is continuously removed during this reaction. Suitable transesterification procedures are described in U.S. Pat. No. 4,104,292, issued to Robert D. Dworkin et al. and in U.S. application Ser. No. 738,138, filed Nov. 2, 1976, the pertinent sections of the aforementioned patent and application are hereby incorporated by reference.

PROCEDURE 8

This method is essentially the same as Procedure 7 except that the mercaptoalkanol is first mixed with water. Ammonium hydroxide or an alkali metal hydroxide is then slowly added to one or more organotin halides while the temperature of the reaction mixture is maintained at from 25° to 65° C.

PROCEDURE 9

This procedure utilizes any of the previous procedures which will generate an organotin mercaptoalkanoate sulfide having one or more free hydroxyl groups. Any water present in the reaction mixture is removed using azeotropic distillation or a distillation under atmospheric or reduced pressure. The residue is reacted with a boron, aluminum, phosphorous, silicon or titanium compound as previously defined, while any reaction by-products such as water and alcohol are removed.

PROCEDURE 10

Mono- and/or diorganotin mercaptoalkanoates having no sulfide groups are prepared by reacting one or more organotin halides with an amount of base sufficient to neutralize the halides, adding the mercaptoalkanoate compounds described in Procedure 7, and optionally one or more additional compounds of the formula $HSR_{43}COOR_{47}$, $HSR_{46}$, $HSZOR_{45}$, $HSCOR_{47}$, $HOCOR_{47}$, $HSCSR_{47}$ or $HOCSR_{47}$, such that the total number of moles of these compounds will stoichiometrically satisfy the organotin oxides and/or hydroxides formed in the above neutralization step, reacting this mixture at about 25° to 75° C. and isolating the resultant organotin product, followed by the addition of a mono- and/or diorganotin sulfide and the redistribution reaction of these organotin compounds at about 25° to 150° C.

In the foregoing formulae $R_{43}$ is alkylene and contains from 1 to 20 carbon atoms, $R_{45}$ is hydrogen, alkyl, substituted alkyl, aryl, aralkyl, alkaryl, aralkenyl, alkenyl, hydroxyalkyl or hydroxyalkenyl, wherein any alkyl residue contains from 1 to 20 carbon atoms and any alkenyl residue contains from 2 to 20 carbon atoms, or $R_{45}$ can represent the residue resulting from removal of the hydrogen atoms from the hydroxyl groups of a polyalkylene glycol or a difunctional hydroxyl-terminated polyether or poly(alkylene oxide). $R_{46}$ is hydrocarbyl (alkyl, aryl, cycloalkyl, aralkyl or alkaryl) which may contain one or more inert substituents, and $R_{47}$ is hydrogen, $R_{46}$ or Q as defined hereinbefore.

These basic procedures are described in more detail in Hoye et al. U.S. Pat. No. 3,609,120. The entire disclosure of Hoye et al. is hereby incorporated by reference. Some of the present compounds can be prepared by following the working examples of Hoye et al. and replacing at least a portion of the mercaptoacid ester compounds employed by Hoye with the mercapto compounds of the formulae shown in Procedure 7.

PROCEDURE 11

This procedure is essentially the same as Procedure 10 except that previously formed mono- and/or diorganotin oxides or hydroxides are substituted for the organotin halide and base of Procedure 10.

The following examples describe the preparation of specific compounds that are within the scope of the present invention or are intermediates therefor and demonstrate the efficacy of these compounds as stabilizers for vinyl chloride polymers. All parts and percentages are by weight unless otherwise specified.

Examples 1–3 and 5 demonstrate the preparation of intermediates which can be further reacted to form compounds within the scope of this invention.

EXAMPLE 1

A 500 cc flask is charged with 80 g (1.0 mole) 2-mercaptoethanol, 125 cc water and 58 g (1.0 mole) aqueous ammonium hydroxide solution. To the above stirred mixture is added 152 g (0.50 mole) liquified dibutyltin dichloride at a rate such that the temperature of the reaction mixture is maintained at or below 60° C. Upon completion of the addition, the reaction mixture is heated at 65° C. and stirred for 30 minutes, after which time the aqueous and organic phases are separated and the aqueous phase is discarded. The organic phase is then concentrated under reduced pressure to yield 178 g of dibutyltin bis(2-hydroxyethylmercaptide), a viscous oil which converts to a semisolid at ambient temperature.

EXAMPLE 2

A 500 cc flask is charged with 58 g (1.0 mole) concentrated aqueous ammonia solution, 125 cc water and 80 g (1.0 mole) of 2-mercaptoethanol. This mixture is stirred during the addition of 94 g (0.33 mole) of monobutyltin trichloride at a rate that maintains the temperature of the reaction mixture between 25° and 60° C. The reaction mixture is heated to 60° C. for ½ hour following completion of the organotin chloride addition, following which the pH of the reaction mixture is adjusted to 7 using ammonium hydroxide to ensure a complete reaction. After this time the aqueous and organic phases are separated, the former is discarded and the organic portion is concentrated under reduced pressure to yield 122 g of monobutyltin tris(2-hydroxyethylmercaptide), which melts at about 60° C.

EXAMPLE 3

A 250 cc flask is charged with 85 g (0.3 mole) monobutyltin trichloride and 90 cc water. To this stirred solution is slowly added 39 g (0.3 mole) solid sodium sulfide at a rate such that the temperature of the reaction mixture is maintained below 60° C. Upon completion of the addition the reaction mixture is heated to 60° C. for one hour. The aqueous phase is then removed and discarded and the organic phase is concentrated under reduced pressure. Monobutyltin chloride sulfide (66 g) is obtained as a viscous liquid.

EXAMPLE 4

A 250 cc flask is charged with 44.5 g (0.06 mole) of the bis(2-mercaptoethyl)ester of Empol ® 1010 Dimer Acid and 17 g (0.06 mole) monobutyltin trichloride. To this mixture is added, with stirring, a solution containing 6.3 g (0.11 mole) concentrated ammonium hydroxide and 20 cc water. The temperature of the reaction mixture increased to 45° C. during the addition. The mixture is then cooled to 40° C. and 3.9 g (0.03 mole) solid sodium sulfide is added slowly. Upon completion of the addition 0.6 g (0.01 mole) concentrated ammonium hydroxide is added and the mixture is heated to 85° C. and held at this temperature for ½ hour. The organic phase containing the desired product is then separated from the aqueous phase, which is discarded. The organic phase is concentrated under reduced pressure to yield 50.3 g of bis[monobutyltin di(2-mercaptoethyl) Empol ® 1010 Dimer Acid] sulfide as a rubbery solid.

EXAMPLE 5

A liter flask is charged with 56.5 g (0.2 mole) monobutyltin trichloride and 90 cc water. To this stirred solution is added 35 g (0.6 mole) of concentrated ammonium hydroxide over 15 minutes. The reaction mixture is stirred for 5 minutes, following which 98 g (0.3 mole) bis(2-mercaptoethyl)azelate are added. The reaction mixture is heated to 90° C., 225 cc of toluene are added and the reaction mixture is heated to 90° C. for ½ hour. The aqueous phase of the reaction mixture is discarded and the organic phase is concentrated under reduced pressure to produce a quantitative yield of bis[monobutyltin]tris[di(2-mercaptoethyl)azelate] as a tacky viscous yellow liquid.

EXAMPLE 6

A 1 liter flask is charged with 113 g (0.4 mole) monobutyltin trichloride, 175 cc water and 32 g (0.4 mole) 2-mercaptoethanol. To this mixture is added, with stirring, 23 g (0.4 mole) of concentrated ammonium hydroxide at a rate that maintains the temperature of the reaction mixture below 60° C. A 52 g (0.4 mole) portion of solid sodium sulfide is then added slowly, following which the pH is adjusted to between 1.5 and 7.0 using ammonium hydroxide, 100 cc toluene are added and the mixture is stirred for 10 minutes. The aqueous phase is then discarded, the organic phase is heated to the boiling point to remove the last traces of water by azeotropic distillation. The reaction mixture is allowed to cool, following which 21 g (0.01 mole) tetraethylorthosilicate are added and the reaction mixture is again heated to the boiling point until 25 cc of distillate are collected in a Dean-Stark trap. The trap is then emptied and 25 cc of toluene are added to the reaction mixture. The replacement of removed distillate with toluene is repeated three more times, at which time all of the solvent is removed under reduced pressure to yield 110 g of tetra(monobutylmonothiotin-2-mercaptoethyl)orthosilicate, a gray, slightly tacky solid. One possible structure for this compound is

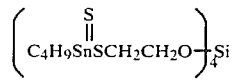

EXAMPLE 7

A 1 liter flask is charged with 56.5 g (0.2 mole) monobutyltin trichloride and 75 cc water. A 11.6 g (0.2 mole) portion of concentrated ammonium hydroxide is then added at a rate such that the temperature of the reaction mixture remains below 55° C. To the resultant mixture is added 33.2 g (0.1 mole) bis(2-mercaptoethyl)azelate and the reaction mixture is heated to 60° C. and maintained at that temperature for about ½ hour, followed by cooling at 40° C. and the gradual addition of 26 g (0.2 mole) of solid sodium sulfide. Once addition is complete the reaction mixture is held at 60° C. for ½ hour, during which time the pH is adjusted to 7 by the addition of ammonium hydroxide. 200 cc of toluene is then added, the aqueous phase is discarded and the organic phase is concentrated. A nearly quantitative yield of bis(monobutylmonothiotin-2-mercaptoethyl)azelate is obtained as a beige, rubbery solid.

EXAMPLE 8

A 2 liter flask is charged with 395 g (1.4 moles) monobutyltin trichloride, 560 cc water and 112 g (1.4 moles) 2-mercaptoethanol, followed by the gradual addition of 81 g (1.4 moles) concentrated ammonium hydroxide and the gradual addition of 182 g (1.4 moles) solid sodium sulfide, the temperature of the reaction mixture being maintained below 60° C. during these additions. The pH is adjusted to 7 using ammonium hydroxide while the reaction is heated to 70° C. for ½ hour. A 116 g (0.7 mole) portion of a mixture containing methyl adipate (90%) and methyl glutarate (10%) is then added, following which the reaction mixture is stirred for 5 minutes. The aqueous phase is discarded and the organic phase is concentrated at 140° C. for 2½ hours under a nitrogen atmosphere to yield 452 g of a viscous, yellow liquid product which consisted mainly of bis(monobutylmonothiotin-2-mercaptoethyl)adipate/glutarate.

EXAMPLE 9

The procedure of Example 6 is repeated substituting 28.5 g (0.1 mole) of tetraisopropyl titanate for the tetraethylortho silicate. The product, a rubbery, brownish-yellow solid is obtained in nearly quantitative yield and contains mainly tetra(monobutylmonothiotin-2-mercaptoethyl)titanate.

EXAMPLE 10

A 1 liter flask is charged with 113 g (0.4 mole) monobutyltin trichloride and 233 cc water, followed by the sequential additions of 46.5 g (0.8 mole) concentrated ammonium hydroxide (temperature maintained between 25° and 45° C.), 32 g (0.4 mole) 2-mercaptoethanol and 65 g (0.2 mole) bis(2-mercaptoethyl)azelate. The reaction mixture is then heated to 70° C. for ½ hour. After cooling to 50° C., 26 g (0.2 mole) solid sodium sulfide are added gradually, following which the reaction mixture is heated to 75° C. for ½ hour. The pH is then adjusted to 7 using ammonium hydroxide. The aqueous phase of the reaction mixture is discarded and the organic portion is concentrated under reduced pressure at a temperature of 100° C. to yield 172 g of viscous liquid that contains bis[monobutyltin(2-hydroxyethylmercaptide)(2-mercaptoethyl)]azelate sulfide as the major component.

EXAMPLE 11

The procedure of Example 7 is repeated substituting an aqueous solution containing 82.5 g (0.2 mole) sodium disulfide for the sodium sulfide. The reaction yielded 78 g of a beige solid, bis(monobutyldithiotin-2-mercaptoethyl)azelate. One possible structure for the compound is

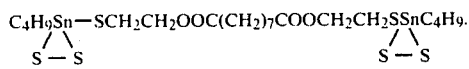

EXAMPLE 12

The procedure of Example 10 was repeated substituting 83 g (0.4 mole) isooctylmercaptoacetate for the 2-mercaptoethanol. The reaction yielded 205 g of a water-white oil consisting mainly of bis[monobutyltin-(isooctylmercaptoacetate)(2-mercaptoethyl)]azelate sulfide.

EXAMPLE 13

A 1 liter flask is charged with 85 g (0.3 mole) monobutyltin trichloride and 150 cc water. An 18 g (0.3 mole) portion of concentrated ammonium hydroxide is gradually added followed by the gradual addition of 39 g (0.3 mole) of solid sodium sulfide. The temperature of the reaction mixture is maintained below 60° C. during these additions. The pH of the reaction mixture is adjusted to 7 using ammonium hydroxide and 100 cc toluene were added. The aqueous phase is discarded and the residual water removed by azeotropic distillation. A 12.4 g (0.1 mole) portion of trimethylphosphite is then added to the cooled solution and the reaction mixture is heated to the boiling point for 178 hour, followed by distillation of 75 cc of an azeotropic methanol-toluene mixture into a Dean-Stark trap. The remaining solvent is removed under reduced pressure. A translucent, nearly colorless, brittle solid is obtained in nearly quantitative yield and consists mainly of tris(monobutyl-monothiotin-2-mercaptoethyl)phosphite.

EXAMPLE 14

The procedure of Example 13 is repeated, substituting 20.4 g (0.1 mole) of aluminum isopropoxide for the trimethylphosphite. The gray solid obtained in nearly quantitative yield consists predominantly of tri(-monobutylmonothiotin-2-mercaptoethyl)aluminate.

EXAMPLE 15

The procedure of Example 10 is repeated, substituting 40.4 g (0.2 mole) n-dodecylmercaptan for one half the stoichiometric amount of 2-mercaptoethanol. A viscous, pale yellow liquid (88 g) is obtained which consists mainly of [monobutyltin(n-dodecylmercaptide)(2-mercaptoethyl-)][monobutyltin(2-hydroxyethylmercaptide)(2-mercaptoethyl-)]azelate sulfide. One possible structure for this compound is

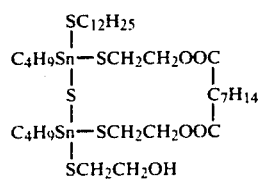

EXAMPLE 16

The procedure of Example 12 is repeated substituting 80 g (0.4 mole) n-dodecylmercaptan for the isooctyl-mercaptoacetate. The product, 119 g of a viscous, colorless oil, contains mainly bis[monobutyltin(n-dodecyl-mercaptide)(2-mercaptoethyl)]azelate sulfide. One possible structure for this compound is

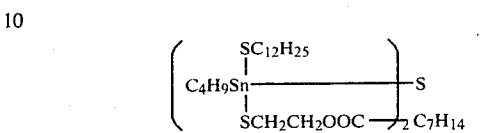

EXAMPLE 17

A 1 liter flask is charged with 70.6 g (0.25 mole) dibutyltin dichloride, 150 cc water and 76 g (0.25 mole) butyltin trichloride. With stirring, 43.5 g (0.75 mole) concentrated ammonium hydroxide is added at a rate which maintains the temperature of the reaction mixture at below 60° C. This is followed by the addition of 162.8 g (0.5 mole) bis(2-mercaptoethyl)azelate and 20 g (0.25 mole) 2-mercaptoethanol. The reaction mixture is then heated to 75° C. for ½ hour. After cooling to 50° C., 32.5 g (0.25 mole) sodium sulfide are added to the mixture at a rate that maintains the reaction mixture temperature below 60° C. Upon completion of this addition the reaction mixture is heated to 75° C. for ½ hour, during which time the pH is adjusted to 7 using ammonium hydroxide. The aqueous phase is discarded, and the organic phase is concentrated under reduced pressure at a temperature of 100° C. and filtered to yield 175 g of a viscous oil. One possible product is [monobutyl-tin-di(2-mercaptoethyl)azelate][dibutyltin-2-hydroxyethylmercaptide]sulfide.

EXAMPLE 18

The procedure of Example 15 is repeated, substituting 34.5 g (0.2 mole) butyl hydrogen maleate for the n-dodecylmercaptan. The reaction yields 170 g of viscous, yellow oil containing mainly [monobutyltin(butyl maleate)(2-mercaptoethyl-)][monobutyltin(2-hydroxyethylmercaptide)(2-mercaptoethyl-)]azelate sulfide.

One possible structure for this compound is

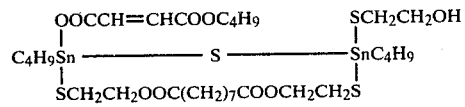

EXAMPLE 19

The procedure of Example 10 is repeated substituting 69 g (0.4 mole) butyl hydrogen maleate for the 2-mercaptoethanol. The reaction yields 180 g of a viscous liquid containing mainly bis[monobutyltin(butyl-maleate)(2-mercaptoethyl)]azelate sulfide.

EXAMPLE 20

The procedure of Example 13 is repeated substituting 10.5 g (0.1 mole) trimethyl borate for trimethyl phosphite. The reaction yields 82 g of a pale yellow solid containing mainly tris(monobutylmonothiotin-2-mercaptoethyl)borate.

EXAMPLE 21

A 1 liter flask is charged with 34.7 g (0.3 mole) monobutyltin trichloride, 130 cc water and 24 g (0.3 mole) 2-mercaptoethanol. An 18 g (0.3 mole) portion of concentrated ammonium hydroxide followed by 39 g of solid sodium sulfide are added at a rate that maintains the temperature of the reaction mixture below 60° C. A 100 cc portion of toluene is then added, the pH is adjusted to 7 using ammonium hydroxide and the reaction mixture is heated for ½ hour at 60° C. The aqueous phase of the reaction mixture is then discarded and residual water is removed from the organic phase by azeotropic distillation. A 36.7 g (0.15 mole) portion of diphenyldimethoxysilane is then added and the reaction mixture heated to the boiling point until 75 cc of an azeotropic solvent mixture are collected in a Dean-Stark trap. The remaining solvent is then removed under reduced pressure until the temperature increases to 100° C. The residual beige, rubbery solid contains mainly bis(-monobutylmonothiotin-2-mercaptoethyl)diphenylsilane.

EXAMPLE 22

The procedure of Example 7 is repated, substituting 74 g (0.1 mole) of the bis-2-mercaptoethyl ester of Empol® 1010 Dimer Acid for the bis(2-mercaptoethyl-)azelate. The procedure yields 111 g of a yellow, rubbery solid that can be represented by the formula

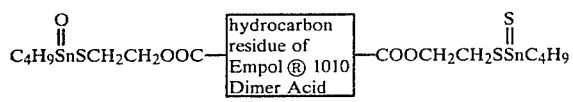

EXAMPLE 23

The procedure of Example 15 is repeated, substituting 41.5 g (0.2 mole) isooctylmercaptoacetate for the n-dodecylmercaptan. This procedure yields 170 g of a viscous, colorless oil that can be represented by the general formula

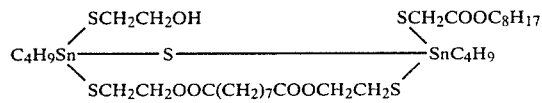

EXAMPLE 24

The procedure of Example 12 was repeated, substituting 81 g (0.4 mole) tertiary dodecylmercaptan for the isooctylmercaptoacetate. The product is 170 g of viscous, colorless oil consisting mainly of a compound that can be represented by the formula

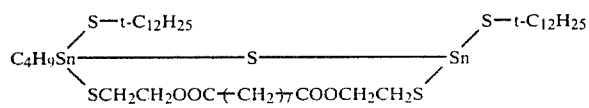

EXAMPLE 25

The procedure of Example 16 is repeated, substituting 67.5 g (0.2 mole) bis(2-mercaptoethyl)adipate for the bis(2-mercaptoethyl)azelate. This procedure yields 196 g of viscous, yellow oil. The expected product can be represented by the formula

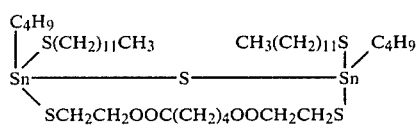

EXAMPLE 26

A 500 cc flask is charged with 113 g (0.4 mole) monobutyltin trichloride and 233 cc water, to which is added 34.8 g (0.6 mole) ammonium hydroxide while the temperature is maintained below 60° C. To this reaction mixture is added 16 g (0.2 mole) 2-mercaptoethanol and 65 g (0.2 mole) bis(2-mercaptoethyl)azelate. The mixture is then heated for ½ hour at 70° C., at which time 26 g (0.2 mole) sodium sulfide are added while the temperature of the reaction mixture is maintained below 75° C. The reaction mixture is then heated for ½ hour at 75° C., the aqueous and organic phases are separated, the aqueous phase discarded and the organic phase is concentrated under reduced pressure to yield 159 g of beige, viscous liquid, the main constituent of which can be presented by the formula

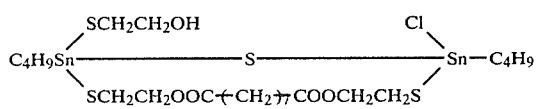

EXAMPLE 27

A 1 liter reactor is charged with 113 g (0.4 mole) monobutyltin trichloride and 300 cc water. A 14.5 g (0.25 mole) portion of ammonium hydroxide solution is added at a rate that maintains the temperature of the reaction mixture below 60° C., followed by rapid addition of 65 g (0.2 mole) bis(2-mercaptoethyl)azelate and 41.5 g (0.2 mole) isooctylmercaptoacetate. The reaction mixture is then heated at 60° C. for ½ hour, after which time 39 g (0.3 mole) solid sodium sulfide is added while the temperature is maintained below 75° C. The reaction mass is then heated at 75° C. for ½ hour while 9 g (0.15 mole) of a 28% aqueous ammonia is added to adjust pH to neutrality. The aqueous phase of the reaction mixture is then discarded and the organic portion is concentrated under reduced pressure until the temperature reached 140° C. A quantitative yield of a viscous, beige oil is obtained. The product can be represented by the formula

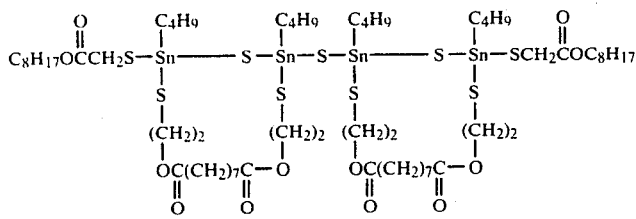

EXAMPLE 28

A 250 cc reactor is charged with 59.2 g (0.045 mole) bis[monobutyltin]tris[di(2-mercaptoethyl)azelate] and 40.8 g (0.045 mole) butylthiostannoic acid. The mixture is stirred and heated to about 100° C. for 1 hour to give a quantitative yield of soft rubbery solid consisting of mainly bis(monobutylmonothiotin-2-mercpatoethyl)azelate.

The advantageous effects of the compounds of this invention as heat stabilizers for vinyl chloride polymers are demonstrated in the following examples. All organotin compounds were used at essentially equal tin concentration, unless otherwise indicated. It is well established that for any given class of organotin stabilizers, e.g. organotin derivatives of mercaptoalkanol esters, the stabilization imparted to poly(vinyl chloride) is directly proportional to the concentration of tin in the composition.

EXAMPLE 29

OVEN STABILITY EVALUATION

Evaluating the compounds of this invention as stabilizers was accomplished by homogeneously blending them into a poly(vinyl chloride) resin composition for about 5 minutes on a two-roll mill at about 160° C. to form a sheet. The composition was then removed from the mill cooled to ambient temperature and cut into 1″×1″ (2.5×2.5 cm) pieces which were placed on trays. The trays were put into a preheated force-air oven at 202° C. Periodically the trays were removed from the oven and samples were evaluated for color development.

The composition of the vinyl chloride polymer formulations employed in the evaluations are as follows:

| FORMULATION I (Clear) | |
|---|---|
| Vinyl chloride homopolymer (Diamond Shamrock PVC-450) | 100.0 |
| Paraffin Wax (XL-165) | 0.5 |
| Stabilizer | As noted |

| OPAQUE FORMULATIONS | | | |
|---|---|---|---|
| | II | III | IV |
| Vinyl chloride homopolymer (Diamond Shamrock PVC-450) | 100.0 | 100.0 | 100.0 |
| Titanium dioxide (Titanox RA-41) | 1.0 | 1.0 | 1.0 |
| Calcium carbonate (Omyalite 90T) | 3.0 | 3.0 | 3.0 |
| Calcium stearate | 0.8 | 0.5 | 1.2 |
| Paraffin wax (XL-165) | 0.5 | 0.5 | 1.0 |
| Stabilizer | | as noted | |

It is evident from the data in Tables 1 and 2 that compounds of this invention which have mercaptoalkanol residues bonded through oxygen to a metallic or non-metallic element rather than to a carboxylic acid provide heat stability to both clear and opaque poly (vinyl chloride) formulations. It is particularly surprising that the stabilization efficacy of these compounds has been found to be at least comparable to prior art products, e.g., Sample #7, which contain sulfide moieties and at least one mercaptoalkyl carboxylic acid ester group linked to tin through the sulfur of the mercaptoalkyl group. This latter class of compounds is alleged to have significant advantages over other prior art stabilizers.

The utility of the compounds of this invention as PVC stabilizers is clearly demonstrated by the evaluation results summarized in Tables 1, 2 and 3. Stabilizer identifications are listed directly following Table 4.

TABLE 1

| Stabilizer No. | PHR[i] | Tin Concentration (mg) | Color Development[ii] with Time (in minutes) at 400° F. | | | | | |
|---|---|---|---|---|---|---|---|---|
| | (Formulation I) | | Initial | 5 | 10 | 15 | 20 | 30 | 40 |
| No stabilizer | | | 3+ | 3 | 2 | 1 | 1 | 1 | 1 |
| 1 | 0.7 | 27.5 | 5 | 5 | 4+ | 4 | 1 | 1 | 1 |
| 2 | 0.7 | 27.2 | 4 | 4 | 4 | 3 | 2 | 1 | 1 |
| 3 | 0.65 | 27.5 | 5 | 5 | 4+ | 4 | 2 | 1 | 1 |
| 4 | 1.5 | 56.1 | 7 | 7 | 6+ | 5− | 3 | 2 | 1 |
| 4 | 0.7 | 26.2 | 7 | 7 | 6 | 5 | 3− | 1 | 1 |
| 5 | 1.5 | 58.1 | 5 | 4+ | 4+ | 4 | 2 | 1+ | 1 |
| 5 | 0.7 | 27.1 | 5 | 4+ | 4+ | 4 | 2 | 1 | 1 |
| 6 | 1.5 | 46.8 | 5 | 4+ | 4+ | 4 | 1+ | 1 | 1 |
| 6 | 0.9 | 28.1 | 5 | 4+ | 4+ | 4 | 1+ | 1 | 1 |
| 13 | 2.7 | 27.0 | 6 | 5 | 4+ | 4 | 1 | 1 | 1 |
| 8 | 2.35 | 27.0 | 6 | 5+ | 5 | 4 | 3 | 1 | 1 |
| 9 | 1.0 | 27.3 | 6+ | 6 | 5 | 4+ | 3 | 1 | 1 |
| 10 | 0.8 | 27.8 | 5+ | 5+ | 5+ | 4+ | 1 | 1 | 1 |
| 11 | 0.9 | 26.6 | 5+ | 5 | 4 | 3 | 2 | 1 | 1 |
| 12 | 1.3 | 27.4 | 7 | 7 | 6 | 5 | 3 | 1 | 1 |
| 25 | 2.7 | 27.0 | 6 | 5 | 4+ | 4− | 1+ | 1 | 1 |
| 14 | 1.1 | 26.9 | 5 | 5 | 4+ | 4 | 2+ | 1 | 1 |
| 15 | 1.0 | 27.5 | 5+ | 5+ | 5 | 4+ | 1 | 1 | 1 |
| 16 | 1.25 | 26.9 | 6 | 5+ | 5 | 4 | 2 | 1 | 1 |
| 17 | 1.15 | 27.6 | 5+ | 5 | 4 | 3 | 1+ | 1 | 1 |

TABLE 1-continued

| Stabilizer No. | PHR[i] | Tin Concentration (mg) | Color Development[ii] with Time (in minutes) at 400° F. | | | | | | |
|---|---|---|---|---|---|---|---|---|---|
| | | | Initial | 5 | 10 | 15 | 20 | 30 | 40 |
| | (Formulation I) | | | | | | | | |
| 18 | 1.6 | 27.1 | 5+ | 5+ | 5 | 4 | 1 | 1 | 1 |
| 19 | 1.0 | 27.0 | 5+ | 5+ | 5 | 4 | 3 | 1 | 1 |
| 20 | 1.1 | 26.5 | 6+ | 6 | 5 | 4 | 3 | 1 | 1 |

[i]PHR — Parts of stabilizer per 100 parts of resin
[ii]Color Scale:
7 — Clear, water-white
5 — Light yellow
3 — Orange to brown
1 — Very dark brown to black
+ Slightly lighter than designated value, but not equal to next higher value
− Slightly darker than designated value, but not equal to next lower value

TABLE 2

| Stabilizer No. | PHR | Tin Concentration (mg) | Color Development[iii] with Time (in minutes) 400° F. | | | | | | |
|---|---|---|---|---|---|---|---|---|---|
| | | | Initial | 5 | 10 | 15 | 20 | 25 | 30 |
| | (Formulation II) | | | | | | | | |
| | No stabilizer | | 3+ | 3 | 2+ | 2 | 2− | 1+ | 1 |
| 7 | 0.5 | 11.8 | 7 | 7 | 6 | 5 | 3 | 2 | 1 |
| 1 | 0.3 | 11.8 | 7 | 7 | 6− | 5− | 3− | 2 | 1 |
| 2 | 0.3 | 11.7 | 7 | 7− | 5+ | 5 | 3 | 2 | 1 |
| 3 | 0.3 | 12.7 | 7 | 7 | 7− | 5 | 3 | 2 | 1 |
| 5 | 0.3 | 11.6 | 7 | 7− | 6− | 5− | 3+ | 2 | 1 |
| 6 | 0.4 | 12.5 | 7 | 7 | 6− | 5 | 3− | 2 | 1 |
| 4 | 0.3 | 11.2 | 7 | 7 | 5+ | 5 | 4 | 2 | 1 |

[iii]Color Scale:
7 — White,
5 — Yellow-White,
3 — Tan to Gray,
1 — Deep Brown

TABLE 3

| Stabilizer No. | PHR | Tin Concentration (mg) | Color Development[iii] with Time (in minutes) at 400° F. | | | | | |
|---|---|---|---|---|---|---|---|---|
| | | | Initial | 4 | 8 | 12 | 16 | 20 | 24 |
| (Formulation III) | | | | | | | | | |
| 8 | 0.53 | 6.1 | 7− | 6+ | 5+ | 5 | 3 | 2 | 1 |
| 9 | 0.20 | 5.5 | 7 | 7 | 6 | 5+ | 3+ | 2 | 1 |
| 12 | 0.28 | 5.9 | 7 | 7 | 6+ | 6 | 3 | 2 | 1 |
| 14 | 0.25 | 6.1 | 7 | 7 | 6+ | 6 | 3 | 2 | 1 |
| 13 | 0.60 | 6.0 | 7 | 7 | 6+ | 6 | 3+ | 2 | 1 |
| 15 | 0.22 | 6.0 | 7 | 7 | 6+ | 6 | 3 | 2 | 1 |
| 24 | 0.21 | 6.0 | 7 | 7 | 6+ | 6 | 3+ | 2 | 1 |
| 16 | 0.28 | 6.0 | 7 | 7 | 6+ | 6 | 3 | 2 | 1 |
| 10 | 0.17 | 5.9 | 7 | 7 | 6 | 5 | 3 | 2 | 1 |
| 11 | 0.20 | 5.9 | 6+ | 6+ | 6 | 5− | 3 | 2 | 1 |
| 17 | 0.25 | 6.0 | 6 | 6 | 5+ | 5 | 3 | 2 | 1 |
| 18 | 0.35 | 5.9 | 7 | 7 | 6 | 5 | 3 | 2 | 1 |
| 19 | 0.22 | 5.9 | 7 | 7 | 6+ | 6 | 3 | 2 | 1 |
| 21 | 0.25 | 6.1 | 7 | 7 | 6 | 5 | 3 | 2 | 1 |
| 22 | 0.24 | 5.9 | 7 | 7 | 6 | 5 | 3 | 2 | 1 |
| 23 | 0.29 | 6.1 | 7 | 7 | 6 | 5+ | 3+ | 2 | 1 |
| 20 | 0.25 | 6.0 | 7 | 7 | 6+ | 5+ | 3 | 2 | 1 |

[iii]Refer to Table 2

BRAEBENDER® DYNAMIC THERMAL STABILITY EVALUATION

The following Brabender® Dynamic Stability Data[iv] (Table 4) exemplifies the kind of superior performance (even at 10% less tin) that one could expect from a typical compound of this invention in comparison to a commercial "state-of-the-art" product:

TABLE 4

| Stabilizer | PHR | Tin Concentration (mg) | Color Development[iii] with Time (in minutes) | | | | | | | |
|---|---|---|---|---|---|---|---|---|---|---|
| | | | 0 | 2 | 4 | 6 | 8 | 10 | 12 | 14 |
| (Formulation IV) | | | | | | | | | | |
| No. 13 | 0.8 | 8.0 | 7 | 7 | 6 | 5 | 5− | 4 | 3 | 1+ |
| Typical Compound of this invention | 0.8 | 8.0 | 7+ | 7 | 7 | 6+ | 5 | 4+ | 3 | 2 |
| | 0.8 | 7.2 | 7 | 7 | 7 | 6+ | 5 | 4 | 3 | 2− |

[iii]Refer to Table 2
[iv]Test method consists of mixing 62 g of stabilized test formulation in a number six mixing head of a C. W. Brabender Torque Rheometer at 200° C. and 60 rpm, while removing small (approx. 5mm × 15 mm) "chips" every two minutes - beginning with fusion - and mounting said chips on a chart for color comparison.

| NUMBER | STABILIZER IDENTIFICATION |
|---|---|
| 1 | Tetra(monobutylmonothiotin-2-mercaptoethyl)-orthosilicate |
| 2 | Tetra(monobutylmonothiotin-2-mercaptoethyl)-titanate |
| 3 | Tris(monobutylmonothiotin-2-mercaptoethyl)-borate |
| 4 | Tris(monobutylmonothiotin-2-mercaptoethyl)-phosphite |
| 5 | Tris(monobutylmonothiotin-2-mercaptoethyl) aluminate |
| 6 | Bis(monobutylmonothiotin-2-mercaptoethyl)-diphenylsilane |
| 7 | Monobutyltin(2-mercaptoethyl-coconut fatty acid ester)sulfide |
| 8 | Bis[butyltin-di(2-mercaptoethyl)Empol 1010 dimerate]sulfide |

| NUMBER | STABILIZER IDENTIFICATION |
|--------|---------------------------|
| 9 | Bis[monobutylmonothiotin-2-mercaptoethyl]azelate |
| 10 | Bis[monobutylmonothiotin-2-mercaptoethyl]-adipate/glutarate |
| 11 | Bis[monobutyldithiotin-2-mercaptoethyl]azelate |
| 12 | Bis[butyltin(isooctylmercaptoacetate)(2-mercaptoethyl)]azelate sulfide |
| 13 | A commercial, diluted methyltin product covered by U.S. Pat. No. 4,062,881 containing 10% tin and 7% sulfur |
| 14 | Bis[(butyltin(isooctylmercaptoacetate)(2-mercaptoethyl)][butyltin(2-mercaptoethyl)]azelate sulfide)sulfide |
| 15 | [Butyltin(isooctylmercaptoacetate)(2-mercaptoethyl)][butylchlorotin(2-mercaptoethyl)]azelate sulfide |
| 16 | Bis[butyltin(n-dodecylmercaptide)(2-mercaptoethyl)]-adipate sulfide |
| 17 | [Butyltin(isooctylmercaptoacetate)(2-mercaptoethyl)][butyltin(2-hydroxyethylmercaptide)(2-mercaptoethyl)]azelate sulfide |
| 18 | Bis[butyltin]tris[di(2-mercaptoethyl)azelate] |
| 19 | Bis[butyltin(2-hydroxyethyl mercaptide)(2-mercaptoethyl)]azelate sulfide |
| 20 | [butyltin(n-dodecylmercaptide)(2-mercaptoethyl)]-[butyltin(2-hydroxyethylmercaptide)]azelate sulfide |
| 21 | [Butyltin(n-butylmaleate)(2-mercaptoethyl)]-[butyltin(2-hydroxyethyl mercaptide)]azelate sulfide |
| 22 | Bis[butyltin-t-dodecylmercaptide)(2-mercaptoethyl)]azelate sulfide |
| 23 | Bis[butyltin(n-dodecylmercaptide)(2-mercaptoethyl)]azelate sulfide |
| 24 | [Butyltin-di(2-mercaptoethyl)azelate] [dibutyltin-(2-hydroxyethylmercaptide)]sulfide |
| 25 | A commercial methyltin/2-mercaptoethanol based product containing 10.2% tin and 10.5% sulfur. |

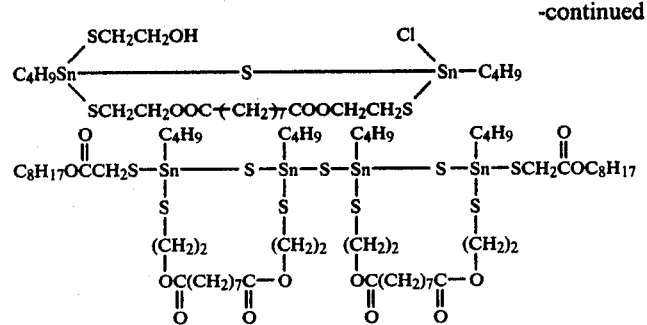

What is claimed is:

1. An organotin compound containing
(a) at least one tin atom having one or two hydrocarbyl, carboalkoxyhydrocarbyl or ketohydrocarbyl groups bonded to tin through carbon, wherein any alkyl portion of said groups contains from 1 to 20 carbon atoms;
(b) at least one mercaptoalkanol residue bonded to tin through the sulfur atom of said residue, the oxygen atom of said residue being bonded to hydrogen, to a hydrocarbyl group, to the residue obtained by removal of the hydroxyl portion of the one carboxy (—COOH) group of a polycarboxylic or hydroxypolycarboxylic acid, or to an element selected from the group consisting of aluminum, boron, phosphorus, silicon and titanium, with the proviso that any polycarboxylic acid is bonded to at least two mercaptoalkanol residues through an oxygen atom of said residue and a carboxyl group of said polycarboxylic acid;
(c) at least one oxygen or sulfur atom, said atom being bonded exclusively to tin or to tin and hydrogen, or at least one polysulfide group that is bonded exclusively to tin;
(d) up to 52% by weight of tin and
(e) up to 63% by weight of sulfur.

2. An organotin compound according to claim 1 wherein said compound exhibits a general formula selected from the group consisting of

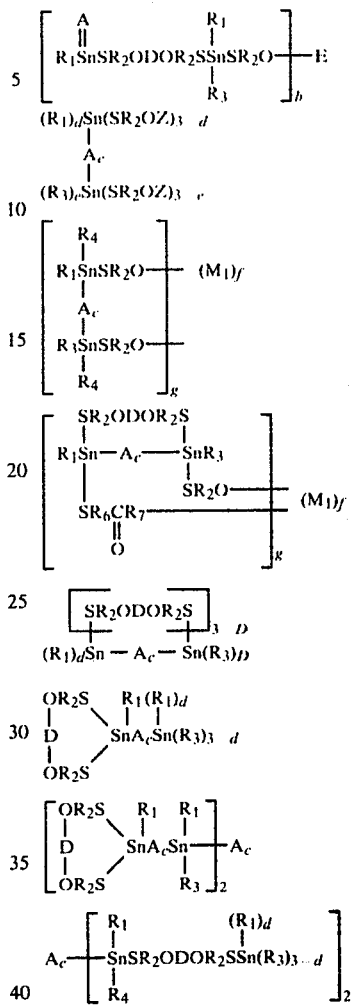

wherein the various terms appearing in said formula are defined as follows:

| Term | Definition |
|------|------------|
| $R_1$ | Hydrocarbyl, carboalkoxyhydrocarbyl or keto-hyrocarbyl wherein any alkyl residue contains from 1 to 20 carbon atoms; if more than one $R_1$ is attached to tin, additional $R_1$ can be halogen, —OH, —SH or residue obtained by removal of active hydrogen from mercaptoacid ester, mercaptan, mercaptoalkanol, monocarboxylic acid or partial ester of a dicarboxylic acid; |
| $R_2$ | Alkylene or arylene group that optionally contains substituent —OX whereas X is hydrogen, aluminum, phosphorus, boron, silicon or titanium; |
| $R_3$ | $R_4$, —$SR_2OZ$ or selected from same group as $R_1$ |
| $R_4$ | $AR_5$, halogen, pseudo-halogen or selected from same group as $R_1$; |
| $R_5$ | —$R_{10}COOR_{11}$ when A is sulfur, $-\overset{O}{\underset{\|}{C}}R_{12}$, $-\overset{S}{\underset{\|}{C}}R_{12}$, —$R_2OZ$, —$R_2OE$, —$R_2OM_1$, —$SnR_{13}R_{14}R_{15}$ or hydrocarbyl selected from same group as $R_1$; |
| $R_6$ | Alkylene containing from 2 to 20 carbon atoms; |
| $R_7$ | Residue obtained by removal of the hydrogen atom from at least two hydroxyl groups of a polyfunctional alcohol containing from 2 to 4 hydroxyl groups; |
| $R_{10}$ | Alkylene or substituted alkylene containing |

-continued

| Term | Definition |
|---|---|
| | from 1 to 20 carbons wherein substituent is halogen, hydroxyl or $-COOR_{11}$; |
| $R_{13}, R_{14}, R_{15}$ | Hydrocarbyl selected from same group as $R_1$; |
| A | Oxygen or sulfur, |
| D | $-OCQCO-$; wherein Q represents a bond between two carbonyl groups or a di- or polyvalent hydrocarbon residue $-(CH_2)_r-$ (r being defined as an integer from 1 to 18), an unsaturated hydrocarbon group, the residue of a di- or polycarboxylic acid or two alkylene groups separated by from 1 to 4 sulfur atoms; |
| $M_1$ | Aluminum, boron, phosphorus, silicon or titanium |
| E | D or $M_1$; |
| a | An integer from 1 to 4; |
| b | An integer from 2 to 4; |
| c | 1 when A is oxygen, 1–10 when a is sulfur; |
| d and e | Each 1 or 2; |
| f | 1 or 2; |
| g | 1, 2, 3 or 4; |
| Z | $M_1$ or $-CQ$  $R_{13}$, wherein h represents an integer from C to 2 |

3. An organotin compound according to claim 2 wherein $R_2$ is alkylene and contains from 2 to 6 carbon atoms.

4. An organotin compound according to claim 2 wherein A is sulfur.

5. An organotin compound according to claim 2 wherein $R_1$ is alkyl and contains from 1 to 8 carbon atoms.

6. An organotin compound according to claim 2 wherein a is 2 or 3 and Z represents the residue of a dimeric, trimeric or tetrameric fatty acid containing 36 to about 72 carbon atoms.

7. An organotin compound according to claim 2 wherein D is $$-CQC-$$

and Q represents an alkylene group containing from 4 to 7 carbon atoms.

8. An organotin compound according to claim 2 wherein $M_1$ is selected from the group consisting of the elements aluminum, boron, phosphorus, silicon and titanium, g is 3 when $M_1$ represents aluminum, boron, or phosphorus and g is 4 when $M_1$ represents silicon or titanium.

9. An organotin compound according to claim 2 wherein $M_1$ is

and g is 2.

10. An organotin compound according to claim 2 wherein said compound is selected from the group consisting of:
bis[monobutyltin di(2-mercaptoethyl)hexatriacontanedioic acid]sulfide
tetra(monobutylmonothiotin-2-mercaptoethyl)orthosilicate
bis(monobutylmonothiotin-2-mercaptoethyl)azelate
bis(monobutylmonothiotin-2-mercaptoethyl)adipate/glutarate
tetra(monobutylmonothiotin-2-mercaptoethyl)titanate
bis[monobutyltin(2-hydroxyethylmercaptide)(2-mercaptoethyl)]azelate sulfide
bis(monobutyldithiotin-2-mercaptoethyl)azelate
bis[monobutyltin(isooctylmercaptoacetate)(2-mercaptoethyl)]azelate sulfide
tris(monobutylmonothiotin-2-mercaptoethyl)phosphite
tri(monobutylmonothiotin-2-mercaptoethyl)aluminate
[monobutyltin(n-dodecylmercaptide)(2-mercaptoethyl-)][monobutyltin(2-hydroxyethylmercaptide)(2-mercaptoethyl-)]azelate sulfide
bis[monobutyltin(n-dodecylmercaptide)(2-mercaptoethyl)]azelate sulfide
[monobutyltin-di(2-mercaptoethyl)azelate][dibutyltin-2-hydroxyethylmercaptide]sulfide
[monobutyltin(butyl maleate)(2-mercaptoethyl-)][monobutyltin(2-hydroxyethylmercaptide)(2-mercaptoethyl-)]azelate sulfide
bis[monobutyltin(butylmaleate)(2-mercaptoethyl)]azeate sulfide
tris(monobutylmonothiotin-2-mercaptoethyl)borate
bis(monobutylmonothiotin-2-mercaptoethyl)diphenylsilane
bis(monobutylmonothiotin-2-mercaptoethyl)azelate

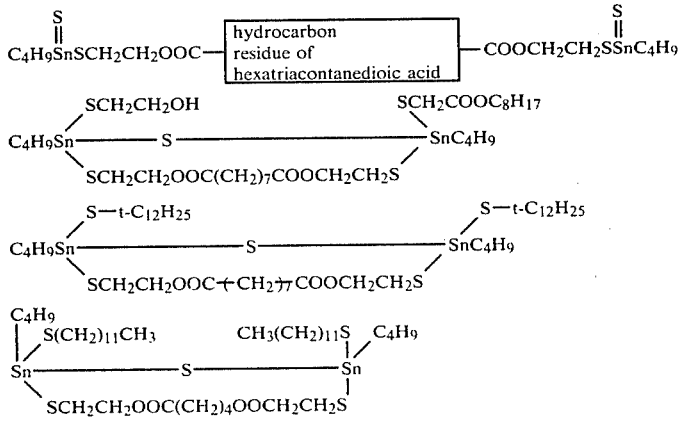

-continued

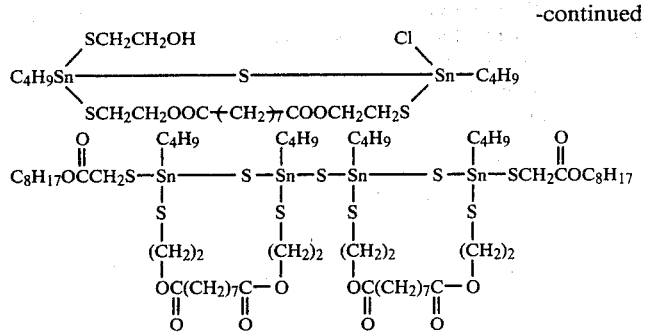

11. A heat stabilized vinyl chloride polymer composition comprising a vinyl chloride polymer and an amount of an organotin compound sufficient to impart resistance to heat-induced degradation to said vinyl chloride polymer wherein the organotin compound contains
    (a) at least one tin atom having one or two hydrocarbyl, carboalkoxyhydrocarbyl or ketohydrocarbyl groups, bonded to tin through carbon, wherein any alkyl portion of said groups contains from 1 to 20 carbon atoms;
    (b) at least one mercaptoalkanol residue bonded to tin through the sulfur atom of said residue, the oxygen atom of said residue being bonded to hydrogen, to a hydrocarbyl group, to the residue obtained by removal of the hydroxyl portion of one carboxy (-COOH) group of a polycarboxylic or hydroxypolycarboxylic acid, or to an element selected from the group consisting of aluminum, boron, phosphorus, silicon and titanium;
    (c) at least one oxygen or sulfur atom, said atom being bonded exclusively to tin or to tin and hydrogen, or at least one polysulfide group that is bonded exclusively to tin;
    (d) up to 52% by weight of tin and
    (e) up to 63% by weight of sulfur.

12. A vinyl chloride polymer composition according to claim 11 wherein said organotin compound exhibits a formula selected from the group consisting of

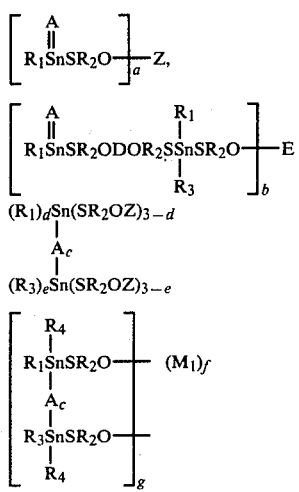

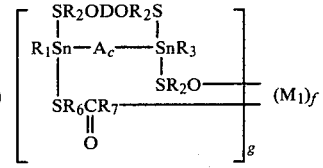

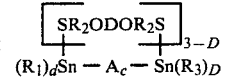

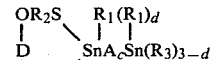

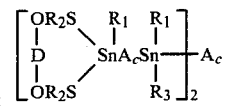

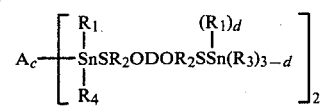

wherein the various terms appearing in said formula are defined as follows:

| Term | Definition |
| --- | --- |
| $R_1$ | Hydrocarbyl, carboalkoxyhydrocarbyl or ketohydrocarbyl wherein any alkyl residue contains from 1 to 20 carbon atoms; if more than one $R_1$ is attached to tin, additional $R_1$ can be halogen, —OH, —SH or residue obtained by removal of active hydrogen from mercaptoacid ester, mercaptan, mercaptoalkanol, monocarboxylic acid or partial ester of a dicarboxylic acid; |
| $R_2$ | Alkylene or arylene group that optionally contains substituent —OX whereas X is hydrogen, aluminum, phosphorus, boron, silicon or titanium; |
| $R_3$ | $R_4$, —$SR_2OZ$ or selected from same group as $R_1$ |
| $R_4$ | $AR_5$, halogen, pseudo-halogen or selected from same group as $R_1$; |
| $R_5$ | —$R_{10}COOR_{11}$ when A is sulfur, —$\overset{O}{\underset{\parallel}{C}}R_{12}$, —$\overset{S}{\underset{\parallel}{C}}R_{12}$, —$R_2OZ$, —$R_2OE$, —$R_2OM_1$, —$SnR_{13}R_{14}R_{15}$ or hydrocarbyl selected from same group as $R_1$; |
| $R_6$ | Alkylene containing from 2 to 20 carbon atoms; |
| $R_7$ | Residue obtained by removal of the hydrogen atom from at least two hydroxyl groups of a polyfunctional alcohol containing from 2 to 4 hydroxyl groups; |
| $R_{10}$ | Alkylene or substituted alkylene containing from 1 to 20 carbons wherein substituent is halogen, hydroxyl or —$COOR_{11}$; |
| $R_{11}, R_{12}$ | Hydrocarbyl groups individually selected from |

-continued

| Term | Definition |
|---|---|
| | same group as $R_1$, and alkenyl containing from 2 to 20 carbon atoms; |
| $R_{13}$, $R_{14}$, $R_{15}$ | Hydrocarbyl selected from same group as $R_1$; |
| A | Oxygen or sulfur; |
| D | $-OCQCO-$, wherein Q represents a bond between two carbonyl groups or a di- or polyvalent hydrocarbon residue $-(CH_2)_r-$ (r being defined as an integer from 1 to 18), an unsaturated hydrocarbon group, the residue of a di- or polycarboxylic acid or two alkylene groups separated by from 1 to 4 sulfur atoms; |
| $M_1$ | Aluminum, boron, phosphorus, silicon or titanium; |
| E | D or $M_1$; |
| a | An integer from 1 to 4; |
| b | An integer from 2 to 4; |
| c | 1 when A is oxygen, 1-10 when A is sulfur; |
| d and e | Each 1 or 2; |
| f | 1 or 2; |
| g | 1, 2, 3 or 4; |
| Z | $M_1$ or $-\overset{O}{\underset{\|}{C}}Q\underset{COOR_2SSn-R_{14}}{\overset{-(COOR_9)_h}{\diagup}}R_{13}$, wherein h represents an integer from 0 to 2. |

13. A vinyl chloride polymer composition according to claim 12 wherein $R_2$ is alkylene and contains from 2 to 6 carbon atoms.

14. A vinyl chloride polymer composition according to claim 12 wherein A is sulfur.

15. A vinyl chloride polymer composition according to claim 12 wherein $R_1$ is alkyl and contains from 1 to 8 carbon atoms.

16. A vinyl chloride polymer composition according to claim 12 wherein a is 2 or 3 and Z represents the residue of a dimeric, trimeric or tetrameric fatty acid containing 36 to about 72 carbon atoms.

17. A vinyl chloride polymer composition according to claim 12 wherein D is $$-\overset{O}{\underset{\|}{C}}Q\overset{O}{\underset{\|}{C}}-$$

and Q represents an alkylene group containing from 4 to 7 carbon atoms.

18. A vinyl chloride polymer composition according to claim 12 wherein $M_1$ is selected from the group consisting of the elements aluminum, boron, phosphorus, silicon and titanium, g is 3 when $M_1$ represents aluminum, boron, or phosphorus and g is 4 when $M_1$ represents silicon or titanium.

19. A vinyl chloride polymer composition according to claim 12 wherein $M_1$ is $$\diagdown_{Si}\diagup\!\!\!\!-\!\!\left(\!\!\bigcirc\!\!\right)_2$$

and g is 2.

20. A vinyl chloride polymer composition according to claim 12 wherein said organotin compound is selected from the group consisting of:

bis[monobutyltin di(2-mercaptoethyl)hextriacontanedioic acid]sulfide
tetra(monobutylmonothiotin-2-mercaptoethyl)orthosilicate
bis(monobutylmonothiotin-2-mercaptoethyl)azelate
bis(monobutylmonothiotin-2-mercaptoethyl)adipate/glutarate
tetra(monobutylmonothiotin-2-mercaptoethyl)titanate
bis[monobutyltin(2-hydroxyethylmercaptide)(2-mercaptoethyl)]azelate sulfide
bis(monobutyldithiotin-2-mercaptoethyl)azelate
bis[monobutyltin(isooctylmercaptoacetate)(2-mercaptoethyl)]azelate sulfide
tris(monobutylmonothiotin-2-mercaptoethyl)phosphite
tri(monobutylmonothiotin-2-mercaptoethyl)aluminate
[monobutyltin(n-dodecylmercaptide)(2-mercaptoethyl)][monobutyltin(2-hydroxyethylmercaptide)(2-mercaptoethyl-)]azelate sulfide
bis[monobutyltin(n-dodecylmercaptide)(2-mercaptoethyl)]azelate sulfide
[monobutyltin-di(2-mercaptoethyl)azelate][dibutyltin-2-hydroxyethylmercaptide]sulfide
[monobutyltin(butyl maleate)(2-mercaptoethyl)][monobutyltin(2-hydroxyethylmercaptide)(2-mercaptoethyl-)]azelate sulfide
bis[monobutyltin(butylmaleate)(2-mercaptoethyl)]azelate sulfide
tris(monobutylmonothiotin-2-mercaptoethyl)borate
bis(monobutylmonothiotin-2-mercaptoethyl)diphenylsilane
bis(monobutylmonothiotin-2-mercaptoethyl)azelate $$C_4H_9SnSCH_2CH_2OOC-\boxed{\text{hydrocarbon residue of hexatriacontanedioic acid}}-COOCH_2CH_2SSnC_4H_9$$
(with S double bonds on each Sn)

$$C_4H_9Sn\underset{SCH_2CH_2OOC(CH_2)_7COOCH_2CH_2S}{\overset{SCH_2CH_2OH}{\diagup}}\!\!-\!\!S\!\!-\!\!\underset{}{\overset{SCH_2COOC_8H_{17}}{\diagdown}}SnC_4H_9$$

$$C_4H_9Sn\underset{SCH_2CH_2OOC-(CH_2)_7COOCH_2CH_2S}{\overset{S-t-C_{12}H_{25}}{\diagup}}\!\!-\!\!S\!\!-\!\!\underset{}{\overset{S-t-C_{12}H_{25}}{\diagdown}}SnC_4H_9$$

$$\underset{Sn}{\overset{C_4H_9}{\big|}}\underset{\diagdown}{\overset{\diagup S(CH_2)_{11}CH_3}{}}\!\!-\!\!S\!\!-\!\!\underset{SCH_2CH_2OOC(CH_2)_4OOCH_2CH_2S}{\overset{CH_3(CH_2)_{11}S\diagdown\ C_4H_9}{\diagup}}Sn$$